United States Patent
Drasler et al.

[11] Patent Number: 6,135,977
[45] Date of Patent: *Oct. 24, 2000

[54] RHEOLYTIC CATHETER

[75] Inventors: William J. Drasler, Minnetonka; Robert G. Dutcher, Maple Grove; Mark L. Jenson, Greenfield; Joseph M. Thielen, Buffalo; Emmanuil I. Protonotarios, Brooklyn Park, all of Minn.

[73] Assignee: Possis Medical, Inc., Minneapolis, Minn.

[*] Notice: This patent is subject to a terminal disclaimer.

[21] Appl. No.: 08/377,995

[22] Filed: Jan. 25, 1995

Related U.S. Application Data

[62] Division of application No. 08/197,051, Feb. 16, 1994, abandoned.

[51] Int. Cl.[7] .................................. A61B 17/20
[52] U.S. Cl. .......................... 604/22; 604/35; 604/43; 606/159
[58] Field of Search .................. 604/22, 27, 30, 604/35, 41, 43–45, 48, 97, 118, 119, 132, 140, 141, 151, 152, 173, 96, 268–269; 128/DIG. 12; 606/159, 167

[56] References Cited

U.S. PATENT DOCUMENTS

| | | |
|---|---|---|
| 1,902,418 | 3/1933 | Pilgrim . |
| 3,930,505 | 1/1976 | Wallach ................................ 604/22 |
| 4,690,672 | 9/1987 | Veltrup ................................ 604/43 |
| 4,790,813 | 12/1988 | Kensey ................................ 604/22 |
| 4,883,459 | 11/1989 | Calderon ................................ 604/28 |
| 4,898,574 | 2/1990 | Uchiyama et al ..................... 604/22 |
| 4,913,695 | 4/1990 | Plechinger et al. ................... 604/43 |
| 4,950,238 | 8/1990 | Sullivan ................................ 604/22 |
| 5,135,482 | 8/1992 | Neracher ................................ 604/22 |

Primary Examiner—Corrine McDermott
Attorney, Agent, or Firm—Hugh D. Jaeger

[57] ABSTRACT

A technique for treatment of plaque deposits on the arterial wall of a patient. The technique employs a high pressure jet of sterile saline solution directed at the plaque deposit. The high pressure jet is located at the distal end of a guide wire or catheter which is advanced through the vascular system to the site of the plaque deposit. Optional removal of the debris is via an evacuation lumen within the catheter. This particular technique directs the high pressure jet of fluid distal to the distal tip of the guide wire or catheter. This permits treatment of arteries, which are totally occluded, because the device need not transit the lesion to be effective. Some applications will use the high pressure jet of fluid to open a sufficient passage within the occlusion to permit further dilatation using a balloon integral to or passed over the device. An ultrasonic transducer array located adjacent the high pressure jet permits the attending physician to monitor the procedure. This may be particularly important for those embodiments for which the high pressure jet of fluid may be inadvertently directed toward the vessel wall at short range. The ultrasound device ensures that the jet of fluid is directed at plaque, rather than the native vessel.

31 Claims, 39 Drawing Sheets

RHEOLYTIC CATHETER

CROSS REFERENCE TO CO-PENDING APPLICATIONS

This application is a division of application Ser. No. 08/197,051, filed Feb. 16, 1994 now abandoned. U.S. patent application Ser. No. 07/563,313, entitled Thrombectomy Method and Device, filed Aug. 6, 1990, in the name of William J. Drasler, et al., and is assigned to the assignee of the present invention and incorporated herein by reference.

BACKGROUND OF THE INVENTION

1. Field of the Invention

The present invention generally relates to medical devices, and more particularly, relates to medical devices for treatment of undesirable deposits within the body of a patient.

2. Description of the Prior Art

Procedures and apparatus have been developed for ease in removing tissue and various deposits. U.S. Pat. No. 4,790,813 issued to Kensey and U.S. Pat. No. 4,842,579 issued to Shiber describe techniques for the removal of plaque deposited in arteries by mechanical ablation using rotating cutting surfaces. These relatively traumatic approaches are directed to the treatment and removal of very hard substances.

Pressurized fluids have also been used in the past to flush undesirable substances from body cavities. U.S. Pat. No. 1,902,418 describes such a system for flushing body cavities of domesticated animals. The more modern references tend to use vacuum rather than gravity as the primary means for removal of the deposits or tissue and relatively low fluid pressures for ablation.

U.S. Pat. No. 3,930,505 issued to Wallach describes a surgical apparatus for the removal of tissue from the eye of a patient. As with similar systems, Wallach uses a relatively low pressure jet of water (i.e. 15 to 3500 psi) to disintegrate the tissue, and a suction pump to perform the actual removal.

A similar approach applied to the cardiovascular system is discussed in U.S. Pat. No. 4,690,672 issued to Veltrup. Veltrup also provides a much lower pressure jet of water (i.e. less than 450 psi) to flush the deposits. As with Wallach, Veltrup uses a vacuum pump for evacuation of the fragments. It seems apparent that the prior art uses only relatively low pressure jets for safety reasons. Furthermore, most of the prior art devices are not suitable to treat fully occluded vessels as they require a portion of the device to transit the lesion.

SUMMARY OF THE INVENTION

The present invention overcomes the disadvantages of the prior art by providing a guide wire or catheter for the treatment of hardened deposits within the cardiovascular system, vascular grafts, ureters, fallopian tubes, and other tubular tissues or cavities with the body using a high pressure jet of sterile saline. The high pressure jet is located at the distal end of the device which is advanced through the tube or cavity to the location of the deposit. The stream of high pressure sterile saline ablates the deposit upon contact. The resulting fragments may be removed through an evacuation lumen. The force of the jet on the evacuation lumen serves as a pump to remove the fragments through the catheter as positive pressure; evacuation does not require a vacuum.

A key aspect of the present invention is that the high pressure jet of fluid is directed distal to the distal tip of the device. For this reason, the device is suitable for treatment of vessels which are fully occluded or nearly fully occluded. To improve monitoring possibilities during the procedure, an ultrasonic transducer array may be appropriately positioned at the distal end of the catheter. The transducer array may be directed toward the deposit or toward a mirror which is in turn directed toward the deposit by way of reflection. Angioscopy, fluorescence spectroscopy, or other monitoring methods may also be used to detect plaque.

The device may employ a single high pressure jet or may use multiple high pressure jets. The jet(s) may be directed parallel to the longitudinal axis of the vessel or may be angled toward or away from the longitudinal axis. Angled jets may be conveniently used to channel particulate material away from the vessel wall and toward the evacuation lumen. The jet(s) may be pulsed or operated at steady state.

A distal balloon may be used to hold the device at the appropriate position within the vessel for ablation of the deposit. This forms the atherectomy function of the device. An additional balloon may also be placed on the device to provide dilation of the vessel. This second balloon provides an angioplasty function for the device.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1A:
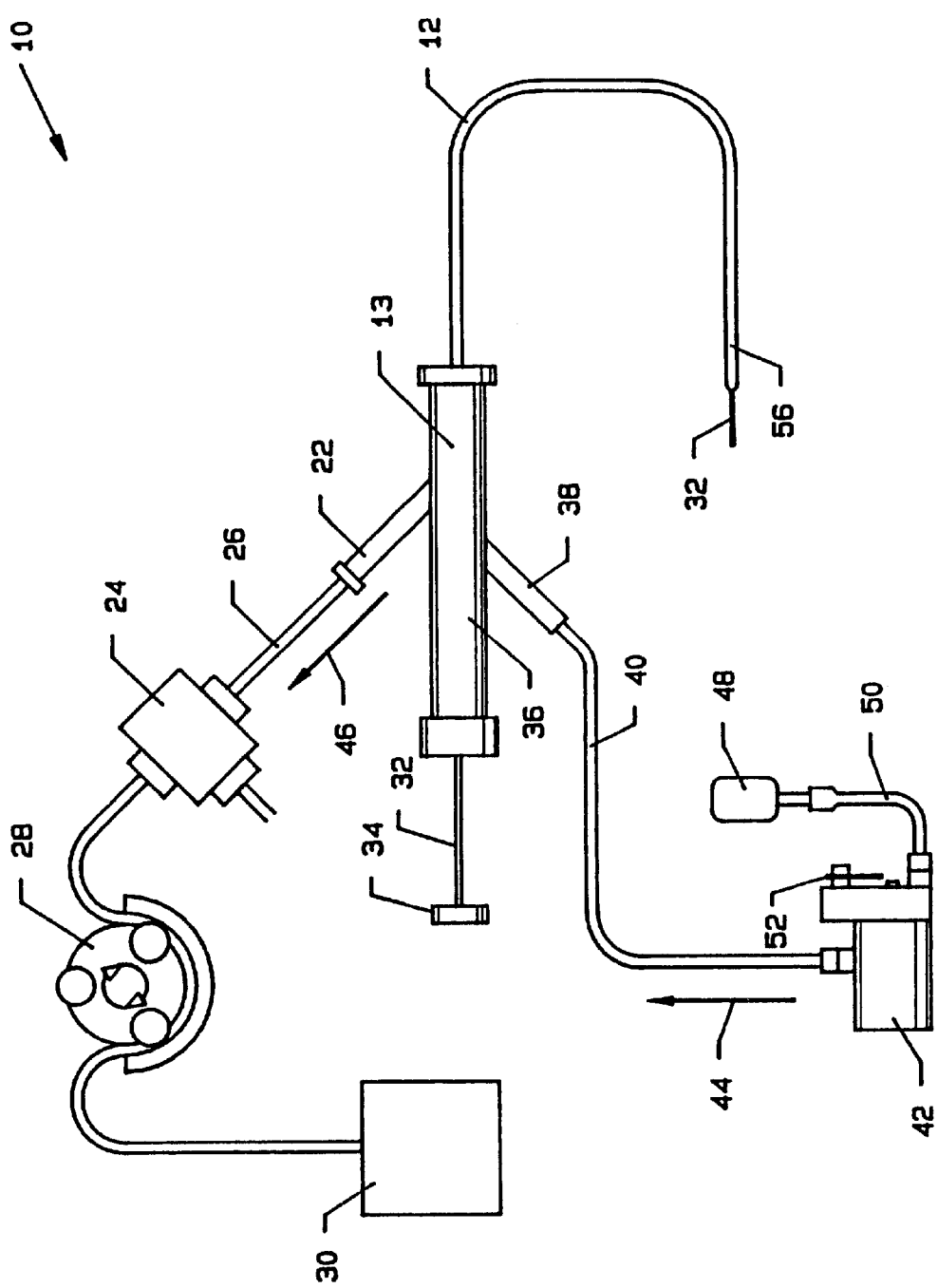
FIG. 1A is a plan view of an atherectomy system employing the present invention.

FIG. 1A is a plan view of a high pressure catheter system 10 employing the present invention. Employing the present invention as a guide wire results in a similar system. However, the catheter application is described by way of example and not to be deemed as limiting, as it tends to be the more complex.

Device body 12 is introduced into an artery of the patient at a convenient location, usually the femoral artery. Distal end 56 is advanced to the site of the deposit to be treated. Ordinarily, this site will have been previously identified using a suitable diagnostic procedure, such as angiography. After location at the site of the deposit, the apparatus at distal end 56 of device body 12 serves to ablate and remove the deposit as explained in more detail below.

Manifold 13 sealingly couples to the proximal end of device body 12 and serves to provide separate access to the various lumens of device body 12. Main branch 36 of manifold 13 sealingly couples to guide wire 32 to assist in positioning device body 12 in the manner known in the art. Note that in systems employing the present invention as a guide wire, guide wire 32 would not be needed. Positioning knob 34 assists the medical attendant in this procedure.

Secondary branch 38 of manifold 13 permits access to device body 12 to supply the sterile saline solution under high pressure. Hypo tubing 40 is drawn from stainless steel to have the strength to handle the pressures up to 50,000 psi, and yet remain flexible enough to be positioned transarterially. Typical pressure is 30,000 psi within the range of 5,000 to 50,000 psi. Hypo tubing 40 traverses the entire length of device body 12 from distal end 56 to secondary branch 38. Preferably, and not by way of limitation, sterile saline is supplied by disposable saline solution bag 48. Low pressure tubing 50 conveys the sterile saline solution to high pressure piston pump 42. After pressurization by high pressure piston pump 42 of typically about 30,000 psi, the sterile saline solution is transported in the direction of arrow 44 through hypo tubing 40 to distal end 56 of device body 12. Safety monitor 52 functions to shut off high pressure piston pump 42 if a failure occurs.

Secondary branch 22 of manifold 13 is coupled to the evacuation lumen of device body 12. Fragments of the ablated deposit are channeled from secondary branch 22 through low pressure tubing 26 in the direction of arrow 46. Safety monitor 24 ensures that the volume of effluent and pressures within the system are maintained within allowable tolerances. Peristaltic pump 28 meters the rate at which effluent is evacuated to disposable bag 30. The environment in which the ablation procedure occurs is greater than one atmosphere due to the impingement of the jet on the evacuation lumen. Peristatic pump 28 meters evacuation of the effluent without ever creating a vacuum.

Figure 1B:
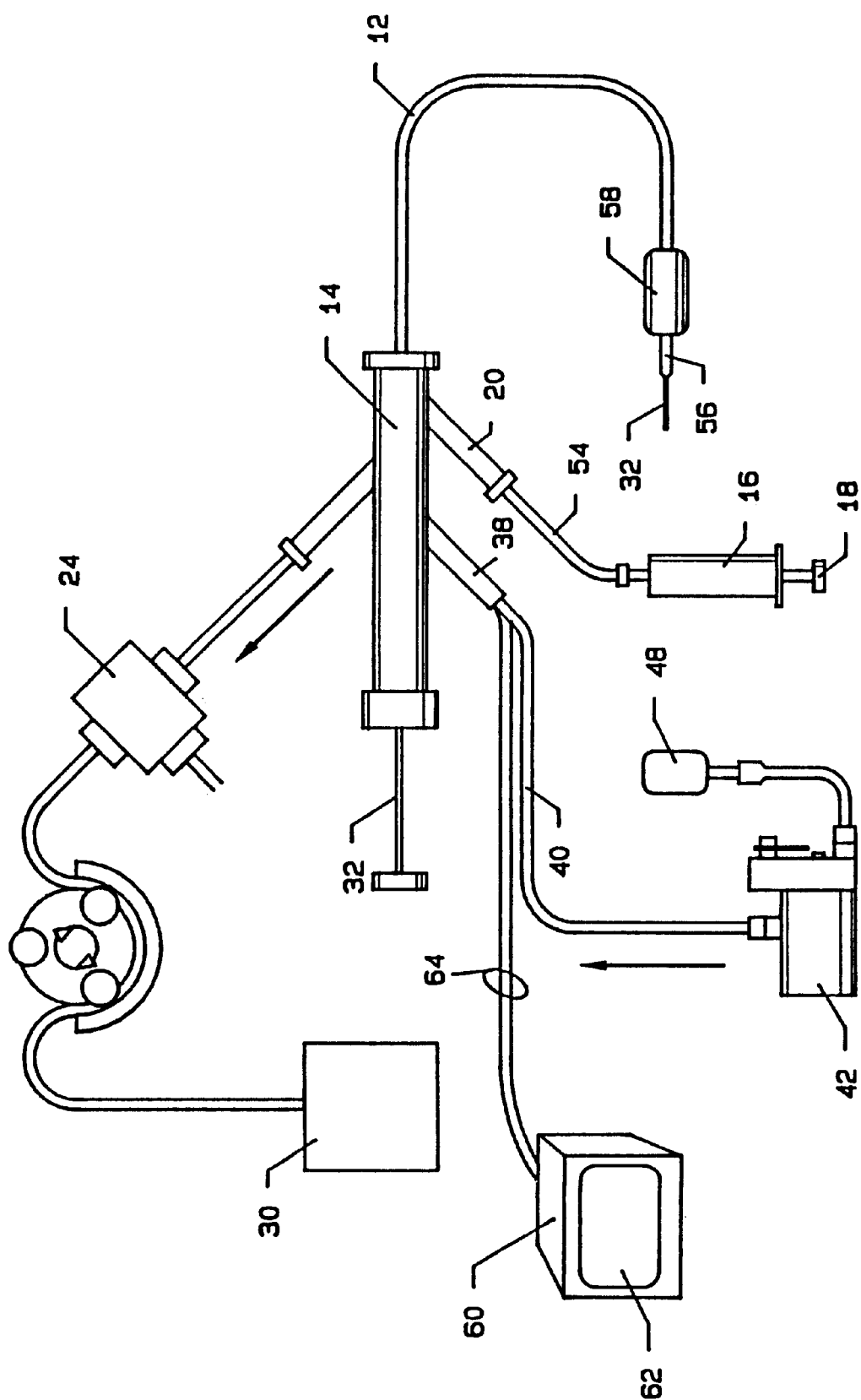
FIG. 1B is a plan view of an atherectomy system having ultrasonic monitoring.

FIG. 1B is a plan view of an alternative embodiment of the present invention. This catheter system includes all of the features of high pressure catheter system 10 with an inflatable distal balloon and ultrasonic monitoring.

Distal balloon 58 may be inelastic such as those used in balloon dilatation, but may also be elastic such as a latex or rubber balloon. The balloon serves to hold the catheter in position to prevent inadvertent impingement of the high pressure jet on the vessel wall. This, or an additional balloon (not shown) located on the distal end of the catheter may be used as a vessel dilatation balloon after removal of the deposited material.

In the alternative embodiment, manifold 13 (see also FIG. 1A) is replaced with manifold 14 having additional secondary branch 20. The inflation lumen of device body 12, which is coupled to distal balloon 58, is sealingly coupled through secondary branch 20 and flexible tubing 54 to balloon inflation device 16. In this way, distal movement of thumb plunger 18 causes inflation of distal balloon 58.

An additional feature of the alternative embodiment is ultrasonic monitor 60 which is coupled via cable 64 to an ultrasonic transducer array (not shown in this view) located at distal end 56. Medical personnel may view the ablation procedure on screen 62 of ultrasonic monitor 60.

Figure 2A:
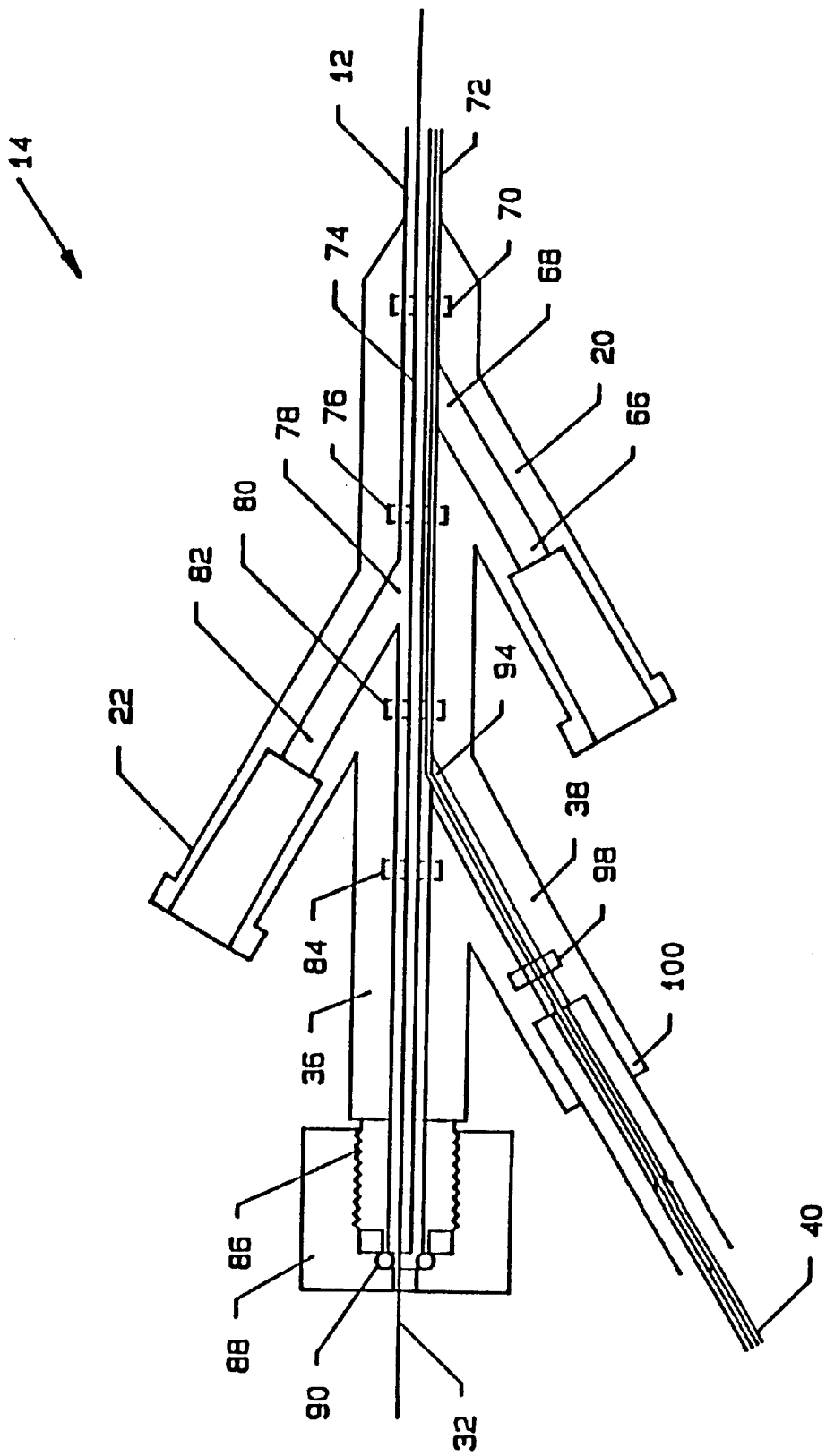
FIG. 2A is a close-up sectioned view of manifold.

FIG. 2A is a longitudinal sectioned view of manifold 14. It is preferably molded from a rigid plastic as two halves which are bonded together and are adhesively coupled to the catheter body 12 and hypo tube 40 at points 70, 76, 80, 84, 98, and 100. Device body 12 is sealingly coupled to the distal end using known techniques.

Lumen 82 of secondary branch 22 is sealingly coupled to evacuation lumen 74. In most embodiments, evacuation lumen 74 will be the largest lumen of device body 12. Evacuation lumen 74 may also be coupled to main branch 36. Compression nut 88 attaches via threads 86 to compress O-ring 90 to sealingly engage guide wire 32. During initial positioning of device body 12, guide wire 32 may be located within evacuation lumen 74.

Lumen 72 contains hypo tubing 40, which enters secondary branch 38, bends obliquely at point 94 and extends the length of lumen 72 distal to point 94.

Also sharing lumen 72 is the function of inflating distal balloon 58. To accomplish this, lumen 66 of secondary branch 20 is coupled to lumen 72 at point 68. Fluid used to inflate distal balloon 58 (see also FIG. 1B) is forced through lumen 72 in that space not occupied by hypo tubing 40.

Figure 2B:
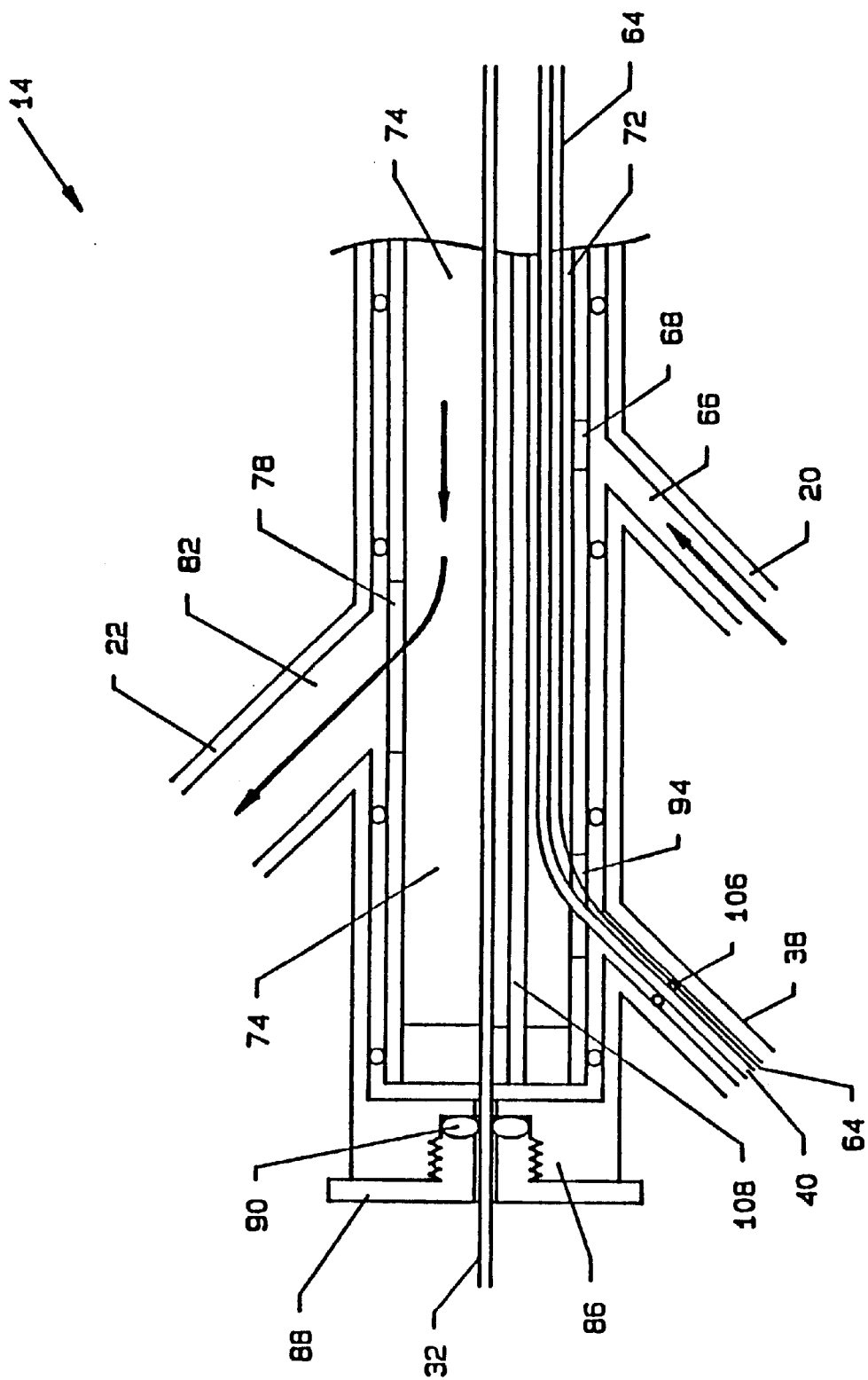
FIG. 2B is a functional view of the manifold having ultrasonic monitoring.

FIG. 2B is a conceptualized view of the operation of manifold 14 wherein all referenced elements are as previously described. In this view it can be seen that septum 108 serves to separate evacuation lumen 74 from lumen 72. Flexible steel 106 seals secondary branch 38 against the walls of hypo tubing 40.

Figure 3A:
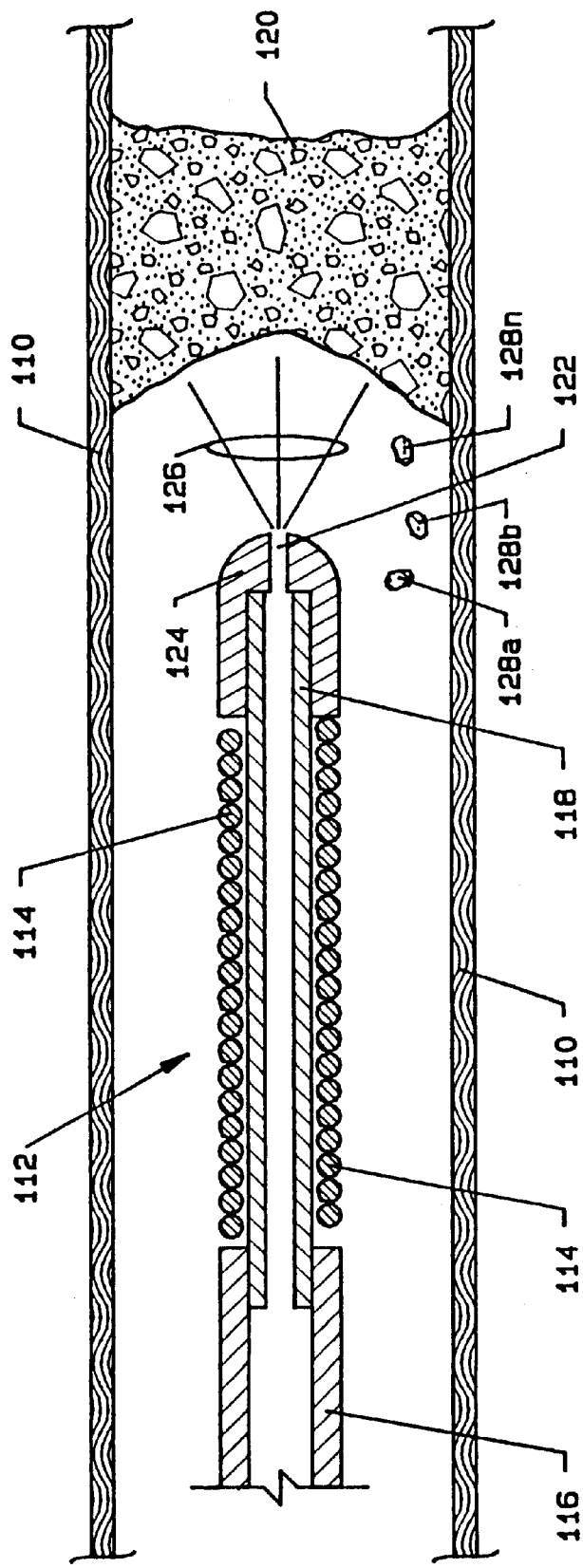
FIG. 3A is a partially sectioned view of the operation of a guide wire according to the present invention.

FIG. 3A is a partially sectioned view of the operation of a rheolytic guide wire 112 employing the present invention. In some respects, this represents the least complex application of the present invention. To be useful, guide wire 112 must have a minimum outside diameter and maximum flexibility.

In the present example, coronary artery 110 is completely occluded by calcified deposit 120. The medical condition cannot be treated using normal percutaneous translumenal coronary angioplasty (i.e. PTCA) because prior art guide wires and catheters are unable to cross the lesion at calcified deposit 120. This may be the case in only partially occluded vessels, as well, if the opening within calcified deposit 120 is too small for a conventional guide wire or catheter.

Guide wire 112 has a main body 116, which is a suitably coated length of stainless steel hypo tubing. It is necessary that the interior lumen of main body 116 have sufficient strength to handle the fluid under pressures up to 50,000 psi, typically about 30,000 psi. To achieve the desired small outside diameter, the hypo tubing of main body 116 is not covered with a separate sheath.

Distal tubing 118 couples main body 116 with nozzle assembly 124. Jet 122 has a diameter of from 0.0003 to 0.004 inch, with a typical diameter of from 0.001 to 0.003 inch. Distal coil 114 encircles distal tubing 118 and provides the desired distal handling characteristics.

In operation, jet 122 is positioned about 0.001 to 0.200 inch from calcified deposit 120. The high pressure fluid is supplied (see also FIGS. 1A and 1B) to produce high pressure stream 126, which abrades calcified deposit 120. Particulate material 128a–128n, which is generally small in size, can be generated from the ablation of plaque. The size of the particulate material is smallest when using a small orifice diameter and is smallest for hard materials, such as calcified plaque. Guide wire 112 has no evacuation lumen such that particulate material 128a–128n must be disposed of by the normal biochemical processes of the patient or other means. Guide wire 112 is advanced during the process until the lesion has been crossed, permitting another dilatation balloon or atherectomy device to be employed.

Figure 3B:
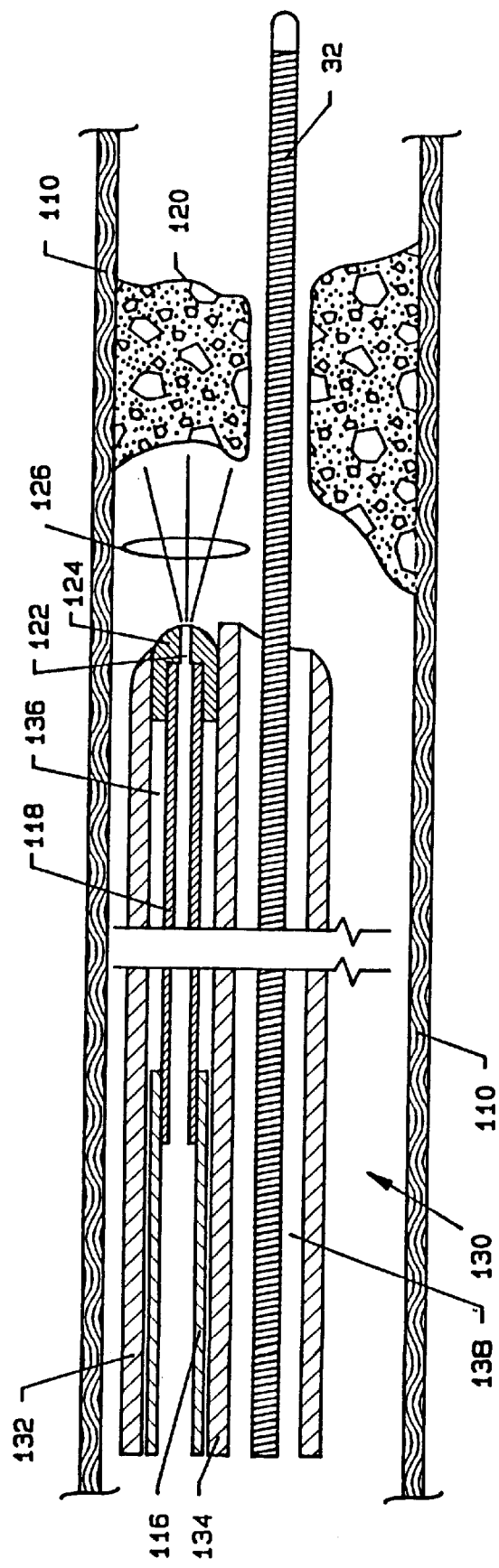
FIG. 3B is a partially sectioned view of the operation of a catheter having a guide wire lumen.

FIG. 3B shows the operation of an atherectomy catheter 130 which is similar to rheolytic guide wire 112, except that it has a guide wire lumen 138. Atherectomy catheter 130 has a much larger outside diameter than guide wire 112. Outer sheath 132 is extruded from a flexible polymer. Septum 134 separates the interior of outer sheath 132 into two lumens. The smaller lumen contains main body 116 of stainless steel hypo tubing as described above. Distal tubing 118 couples main body 116 to nozzle assembly 124 containing jet 122. High pressure stream 126 is produced in the manner described above.

The second and larger lumen formed within outer sheath 132 by septum 134 is guide wire lumen 138. This lumen is coupled to the manifold evacuation as explained above (see also FIGS. 1A and 1B). It contains guide wire 32.

Note that because high pressure stream 126 is directed distal of the most distal point of atherectomy catheter 130, coronary artery 110, which is fully occluded by calcified deposit 120 may be treated in this manner. However, because the outside diameter of guide wire 112 is much smaller (see also FIG. 3A), guide wire 112 can be used for smaller diameter vessels. This device may have a balloon attached for dilatation following the removal of plaque.

Figure 3C:
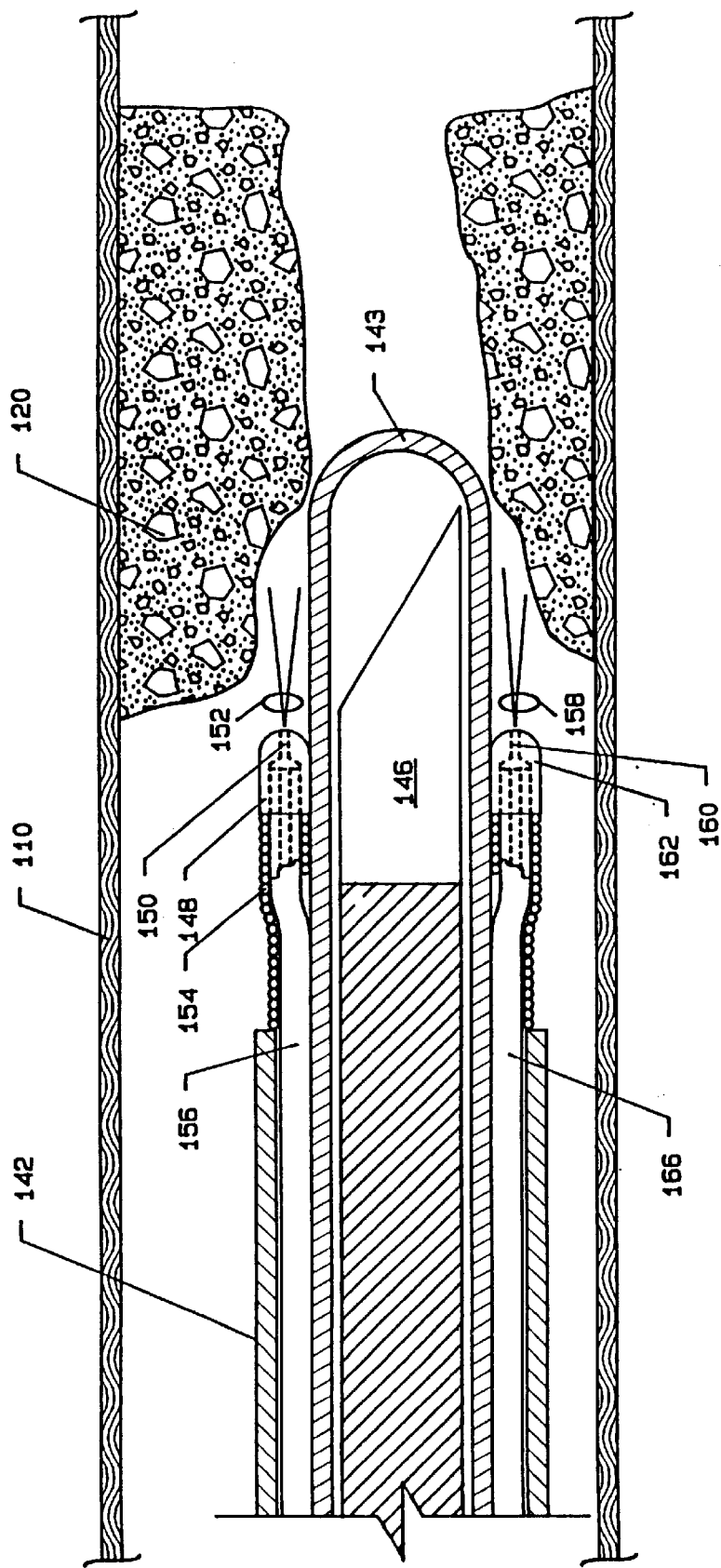
FIG. 3C is a partially sectioned view of the operation of a device having multiple high pressure jets.

FIG. 3C is a partially sectioned view of the operation of a much larger catheter 142 employing multiple high pressure jets. This embodiment is well suited to treat conditions wherein calcified deposit 120 does not fully occlude coronary or peripheral artery 110, but can also be used to open completely occluded vessels. Distal tip 143 is advanced into the narrow lumen within calcified deposit 120, thus positioning the multiple jets around the periphery of calcified deposit 120. This configuration works well if the narrow lumen of calcified deposit 120 is centrally located and/or the multiple jets are individually controlled as is discussed in greater detail below.

To properly control the process, catheter 142 may contain an ultrasonic transducer array 146. The configuration shown requires a larger outside diameter of the outer sheath than the embodiments previously described. Only shown in this view are two of the multiple high pressure jets. High pressure stream 152 is produced by jet 150 of nozzle assembly 148. Fluid communication is provided by hypo tubing 156 coupled to nozzle assembly 148. Similarly, high pressure stream 158 is produced by jet 160 of nozzle assembly 162. Hypo tubing 166 is coupled directly to nozzle assembly 162. Overwrap 154 is used to provide uniform diameter to the nozzle assembly.

Figure 3D:
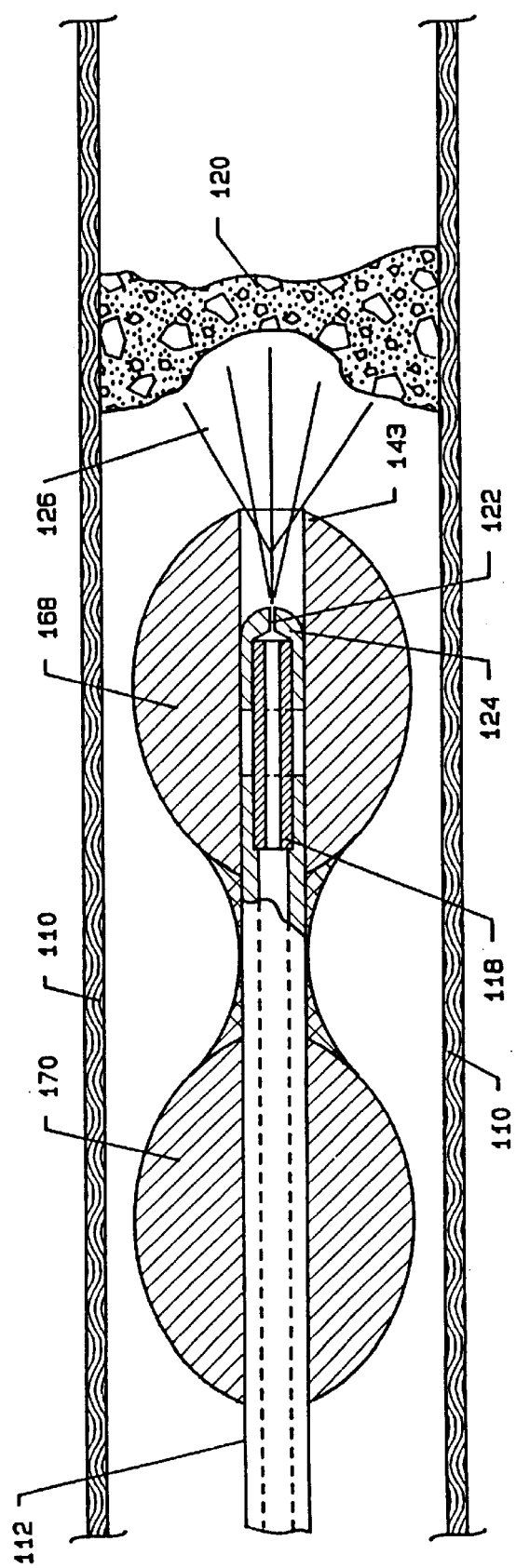
FIG. 3D is a partially sectioned view showing the operation of a guide wire having positioning bulbs.

FIG. 3D is a view of the operation of a bulbous guide wire device having a pair of positioning bulbs 168 and 170. These positioning bulbs are fitted over rheolytic guide wire 112, for example, to ensure that high pressure stream 126 is not inadvertently directed against the walls of coronary artery 110. As can be seen, this restricts high pressure stream 126 to operate upon only the small central portion of calcified deposit 120. This device can be advantageously used preparatory to the use of catheter 142 (see also FIG. 3C). The small lumen abraded through calcified deposit 120 can be used for insertion of distal tip 143. The combination of these two devices permits treatment of coronary artery 110 having a complete occlusion, yet provides safety features to protect the walls of coronary artery 110.

Figure 3E:
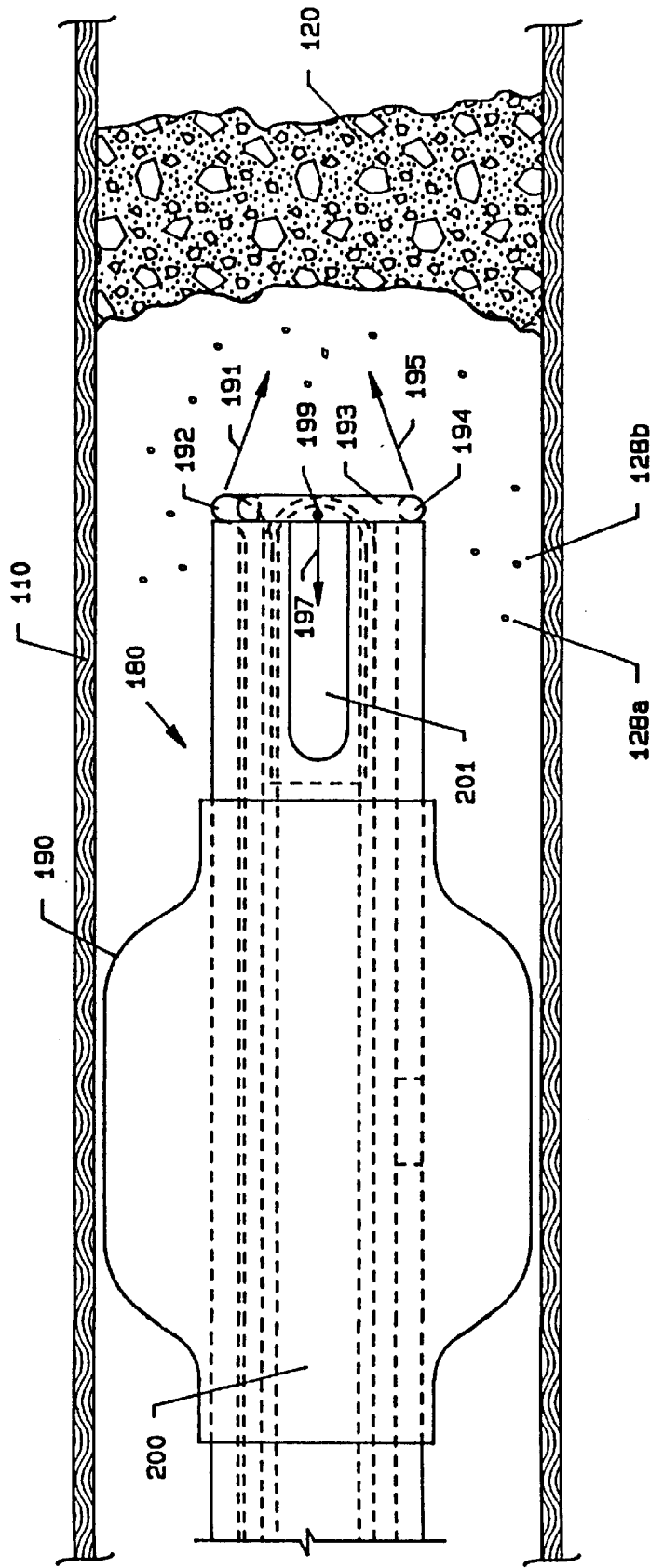
FIG. 3E is a partially sectioned view of the operation of a device having multiple high pressure jets and an evacuation lumen.

FIG. 3E is a view of the operation of a catheter 180 having an inflatable distal balloon 190. This balloon can be used to properly position and maintain the distal tip of catheter 180 to prevent inadvertent impingement of a high pressure jet against the wall of coronary artery 110. Balloon 190, if made of inelastic materials, may also be used for vessel dilatation as in balloon angioplasty. Note that the inflated balloon 190 also tends to prevent proximal flow of particulate material. Two to ten forward shooting jets, shown as 192 and 194, ablate plaque distal to the catheter. A rearward shooting jet 199 is directed as per arrow 197 into the evacuation port 201, which is coupled to evacuation lumen 200. The rearward jet generates a stagnation pressure, which drives flow out of the evacuation lumen. This device can contain a separate channel which will allow passage of an ultrasonic device to the distal tip in order to detect plaque.

Figure 4:
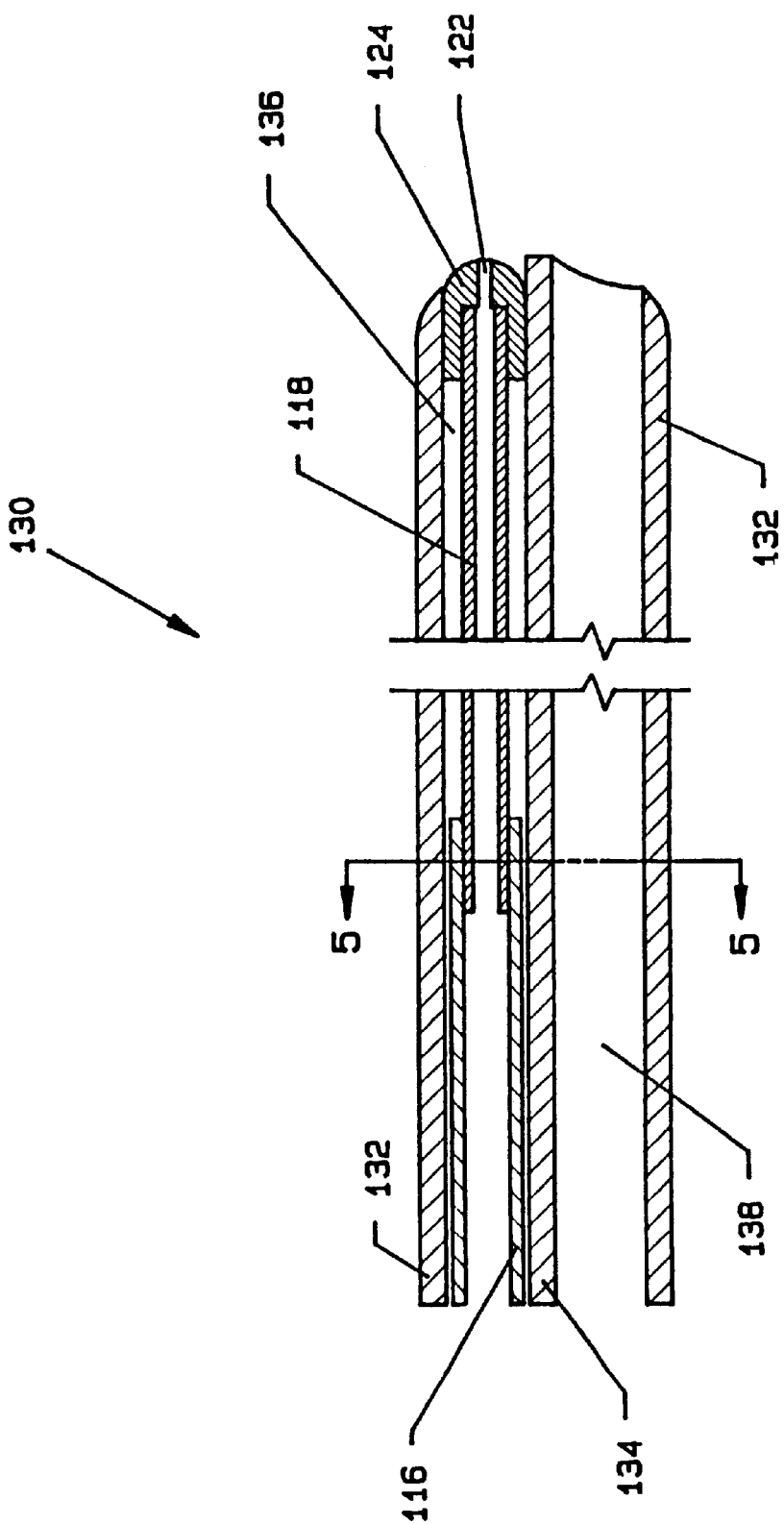
FIG. 4 is a sectioned view of the distal tip of a catheter having a guide wire lumen.

FIG. 4 is a longitudinally sectioned view of atherectomy catheter 130 having a single jet 122 and guide wire lumen 138. Operation is as previously described (see also FIG. 3B).

Figure 5:
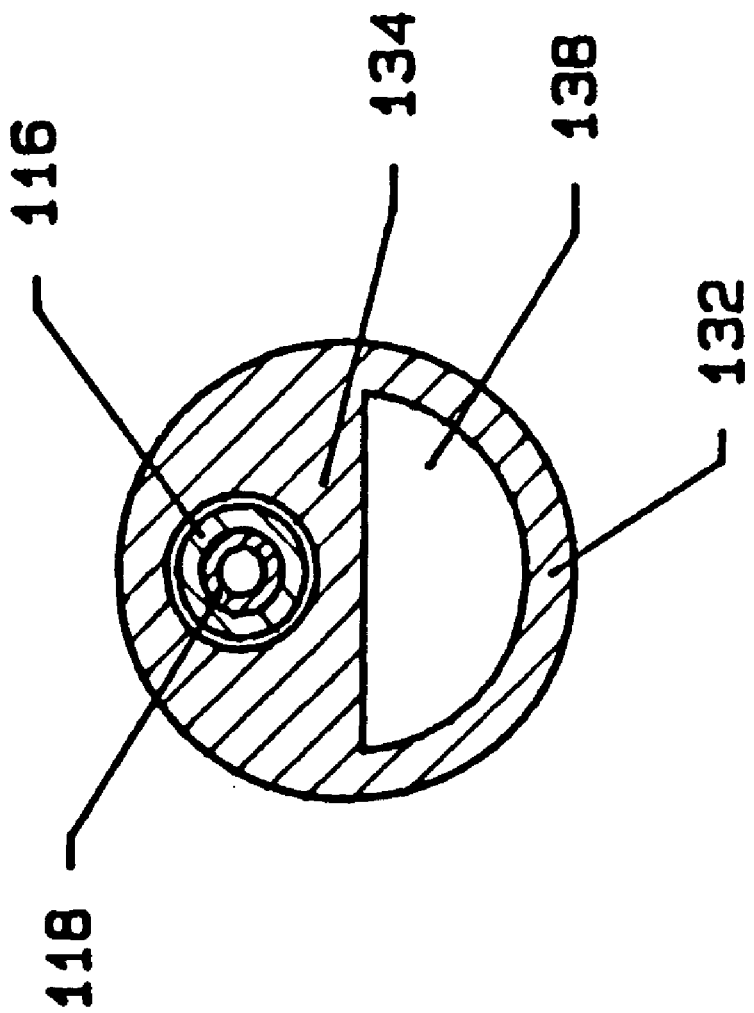
FIG. 5 is a transverse sectioned view of the catheter of FIG. 4.

FIG. 5 is a transverse sectioned view of atherectomy catheter 130. All referenced elements are as previously described.

Figure 6:
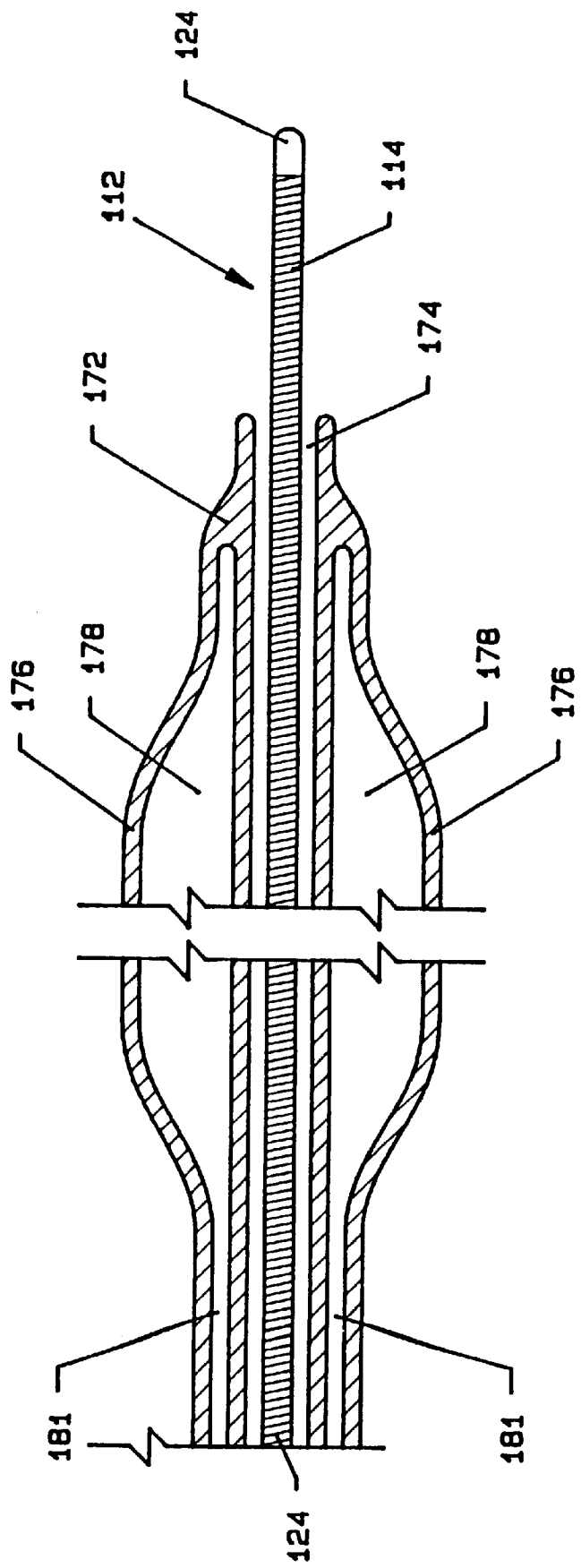
FIG. 6 is a partially sectioned view of a guide wire according to the present invention in use with a standard dilatation balloon catheter.

FIG. 6 is a partially sectioned view of guide wire 112 having a dilatation balloon catheter 182 passed over it. Guide wire 112 assumes its position in large central lumen 174. Outer concentric lumen 181 is employed to inflate dilatation balloon 176 by filling space 178 with a sterile saline solution under low pressure (e.g. 300 psi) in known manner.

Figure 7:
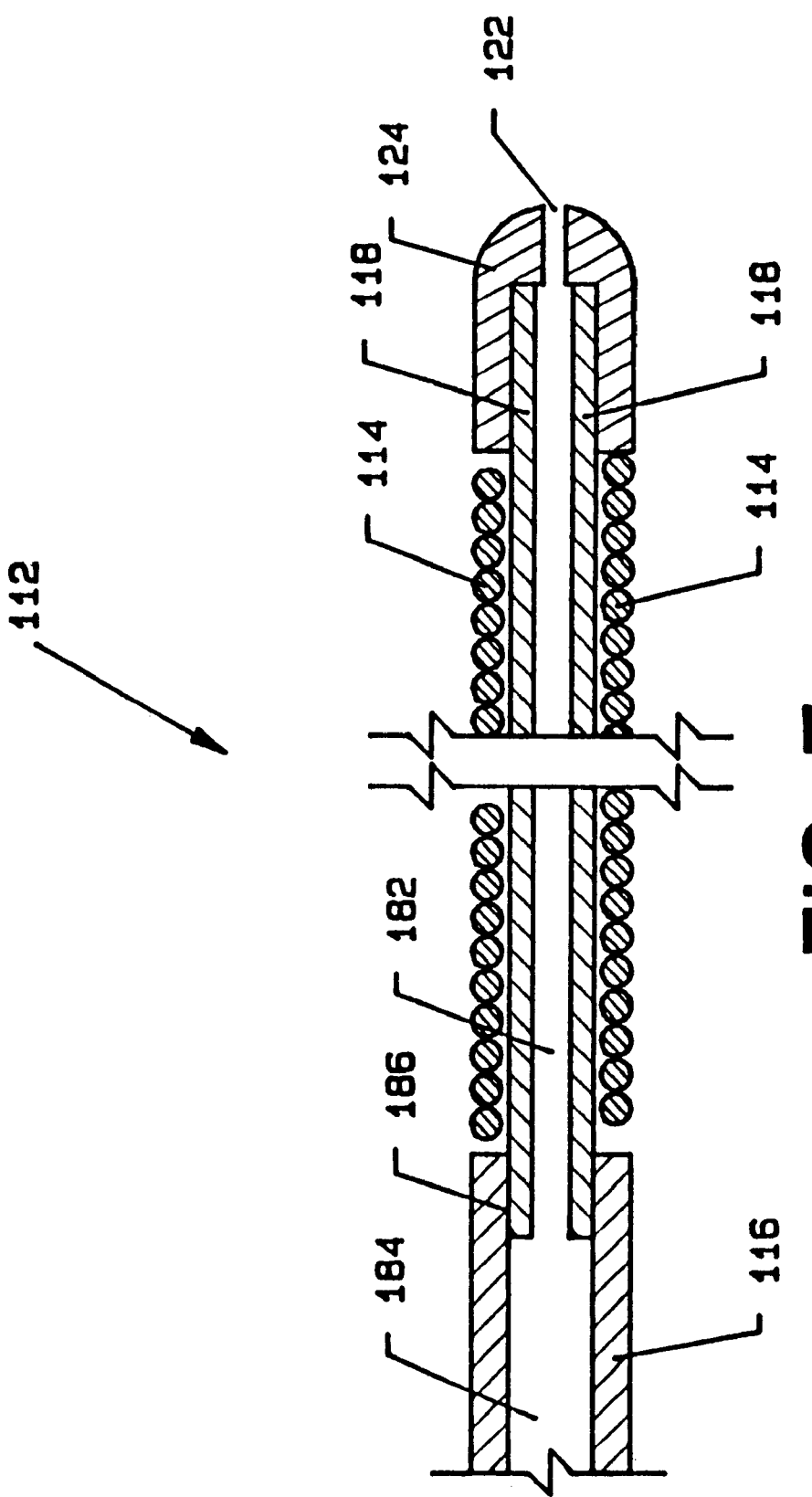
FIG. 7 is a longitudinal sectioned view of the distal tip of a guide wire having a single high pressure jet and no evacuation lumen.

FIG. 7 is a longitudinally sectioned view of the distal end of guide wire 112. All referenced elements are as previously discussed. Lumen 184 of main body 116 has a diameter of about 0.003 to 0.009 inch which is about three times the diameter of jet 122. Distal tubing 118 is welded or brazed to main body 116 at point 186.

Figure 8:
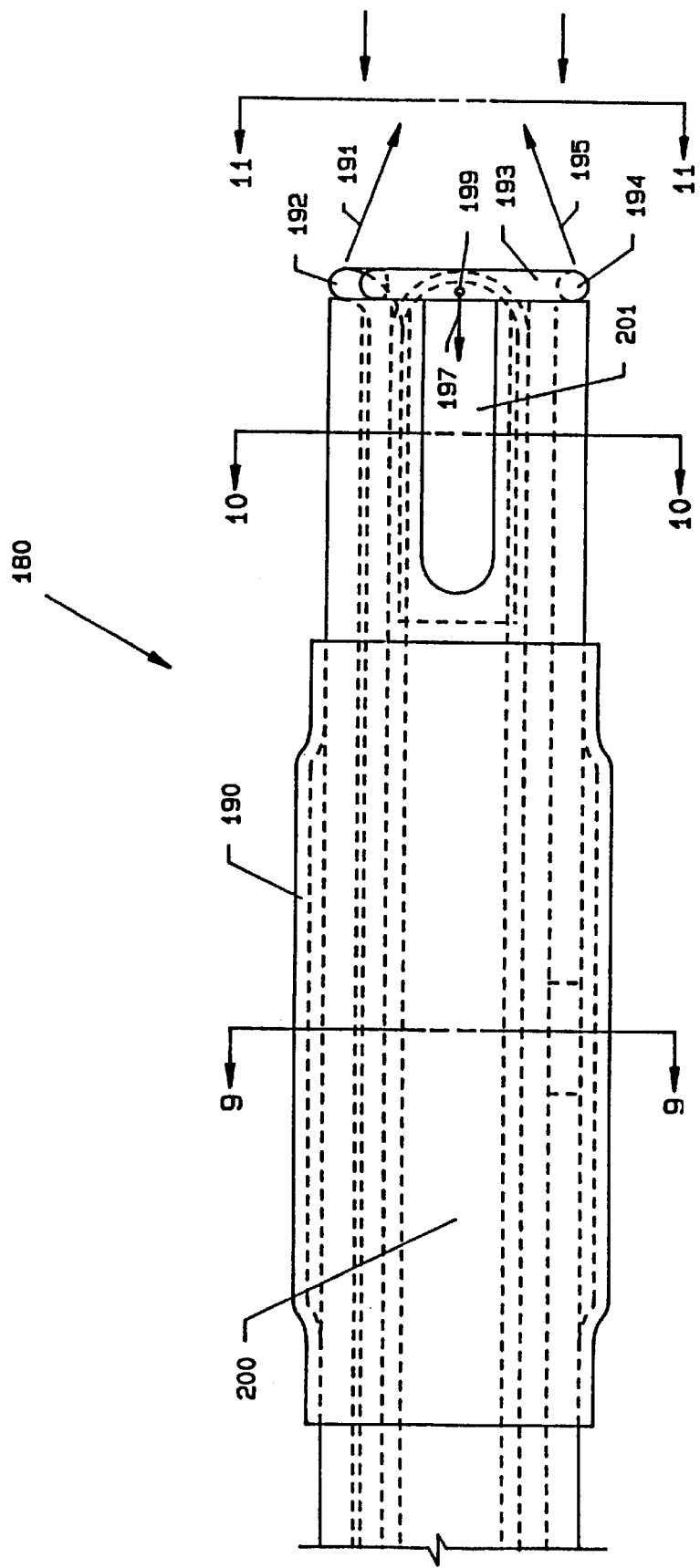
FIG. 8 is a view of the distal tip of a catheter having multiple high pressure jets and an inflatable balloon.

FIG. 8 is a view in partial phantom of the distal end of a catheter 180 employing the present invention. Catheter 180 has a balloon 190 for dilatation and/or positioning and a multiple jet nozzle assembly 193 containing at least jets 192 and 194. It can be seen that though jets 192 and 194 direct their respective streams in a generally distal direction, the streams are angled toward the central longitudinal axis of catheter 180 as shown by arrows 191 and 195. This may be done as a safety feature to protect the vessel walls. Jet 199 is directed rearward as per arrow 197 into the evacuation port 201 for removal through evacuation lumen 200.

Figure 9:
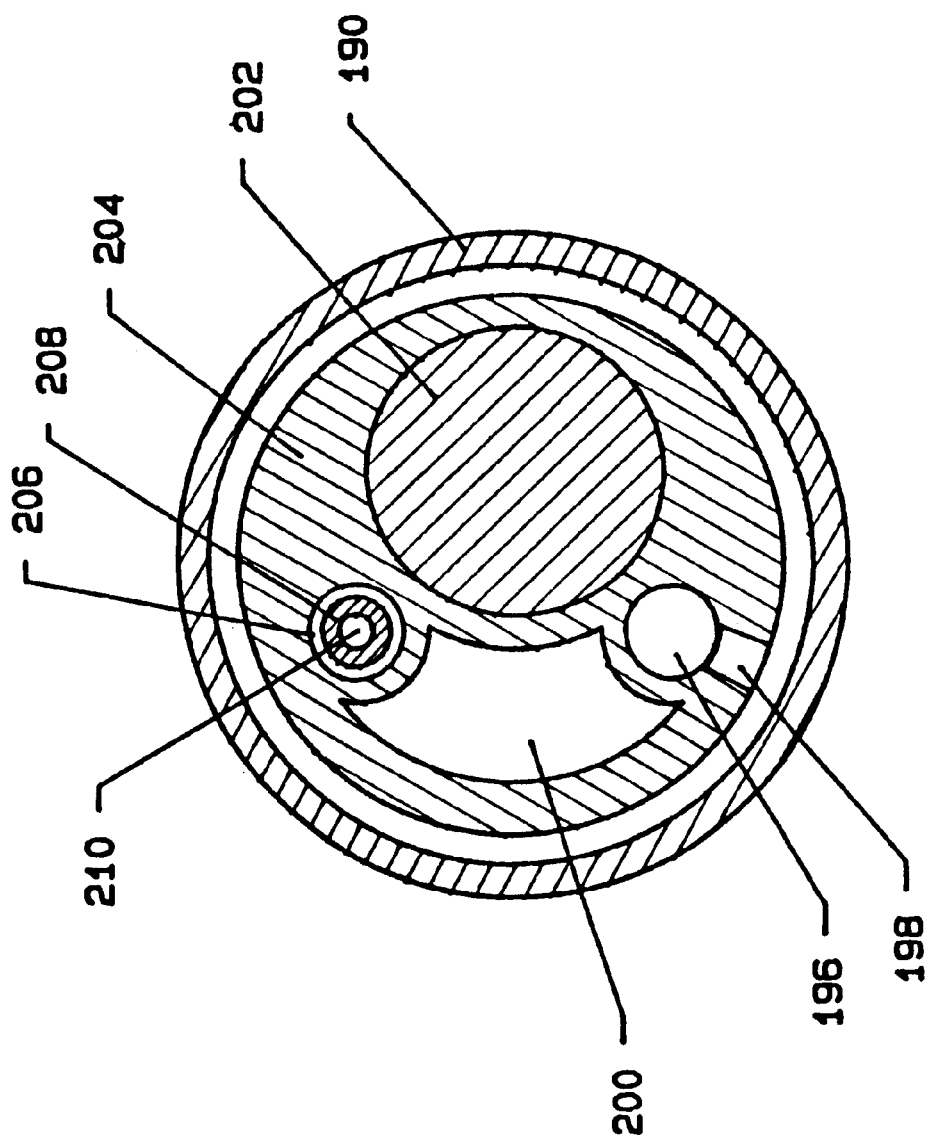
FIG. 9 is a transverse sectioned view of the catheter of FIG. 8 taken across the inflatable balloon.

FIG. 9 is a transverse sectioned view of catheter 180. Lumen 196 is used to inflate balloon 190 through inflation port 198. Evacuation lumen 200 is extruded in an irregular shape as shown. Small lumen 206 accommodates hypo tubing 208 having interior lumen 210. Catheter body 204 also has a large lumen which provides space for ultrasound device 202.

Figure 10:
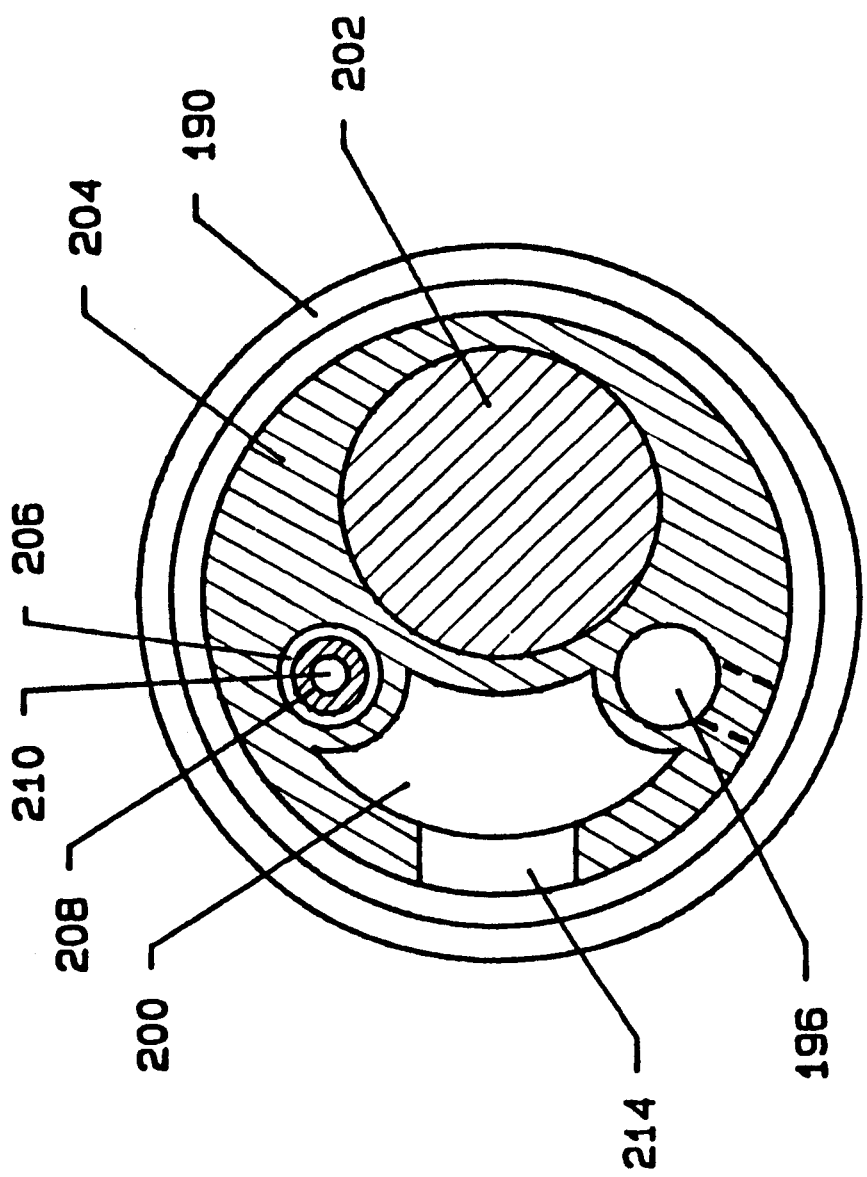
FIG. 10 is a transverse sectioned view of the catheter of FIG. 8 taken distal of the inflatable balloon.

FIG. 10 is a transverse sectioned view of catheter 180 taken distal to FIG. 9. Evacuation port 214 provides side access to evacuation lumen 200. All other referenced elements are as previously described.

Figure 11:
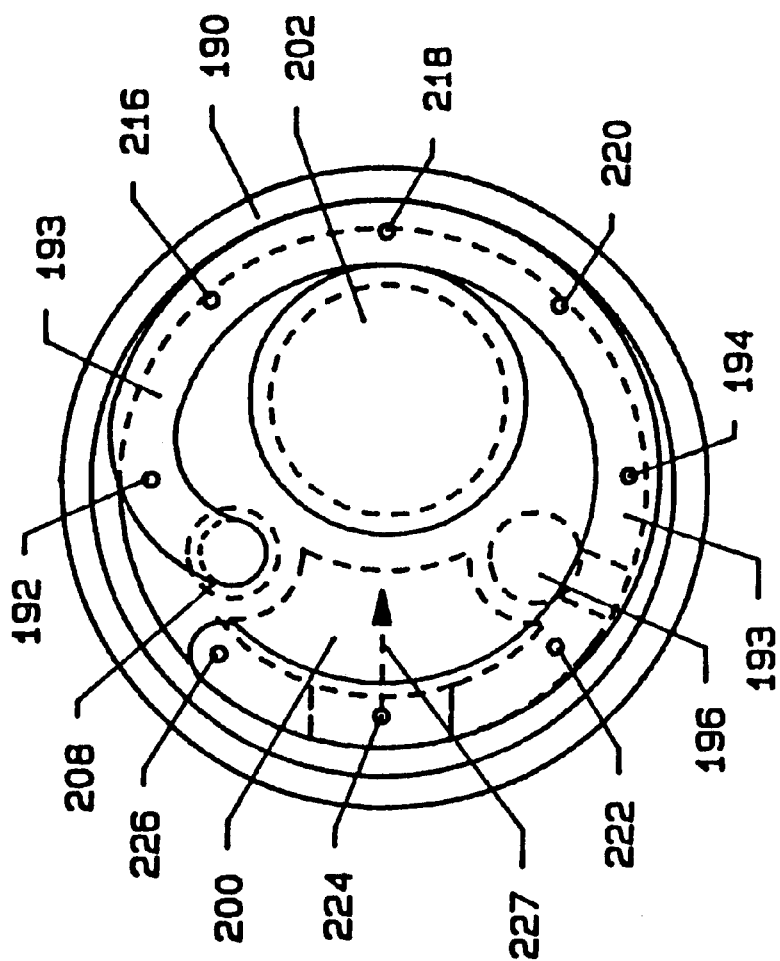
FIG. 11 is a view of the catheter of FIG. 8 taken from the distal end.

FIG. 11 is a view of catheter 180 taken from the distal end. Multiple jet nozzle assembly 193 has individual jets 192, 216, 218, 220, 194, 222, 224, and 226 all supplied from a single source of high pressure fluid (i.e. interior lumen 210 of hypo tubing 208). This does not permit the jets to be individually controlled. The individual jets 192, 216, 218, 220, 194, 222, and 226 are directed distal to the catheter in a converging pattern. Jet 224 is directed proximally as per arrow 227 into the evacuation lumen 200. Particulate material is removed due to the flow generated by this jet. All other referenced elements are as previously discussed.

Figure 12:
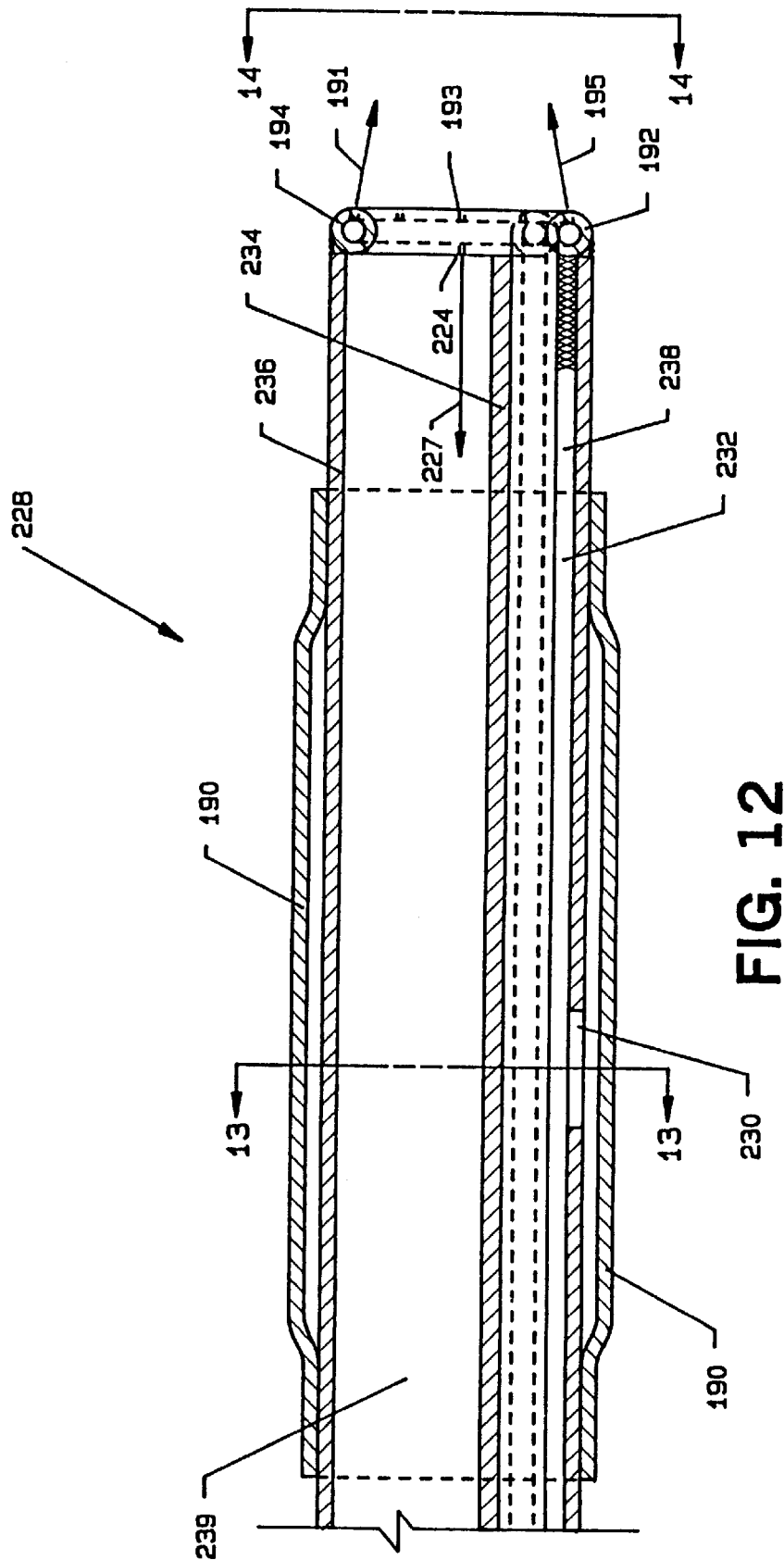
FIG. 12 is a view of the distal end of a catheter having multiple jet, an inflatable balloon, an evacuation lumen, and a guide wire lumen.
Figure 14:
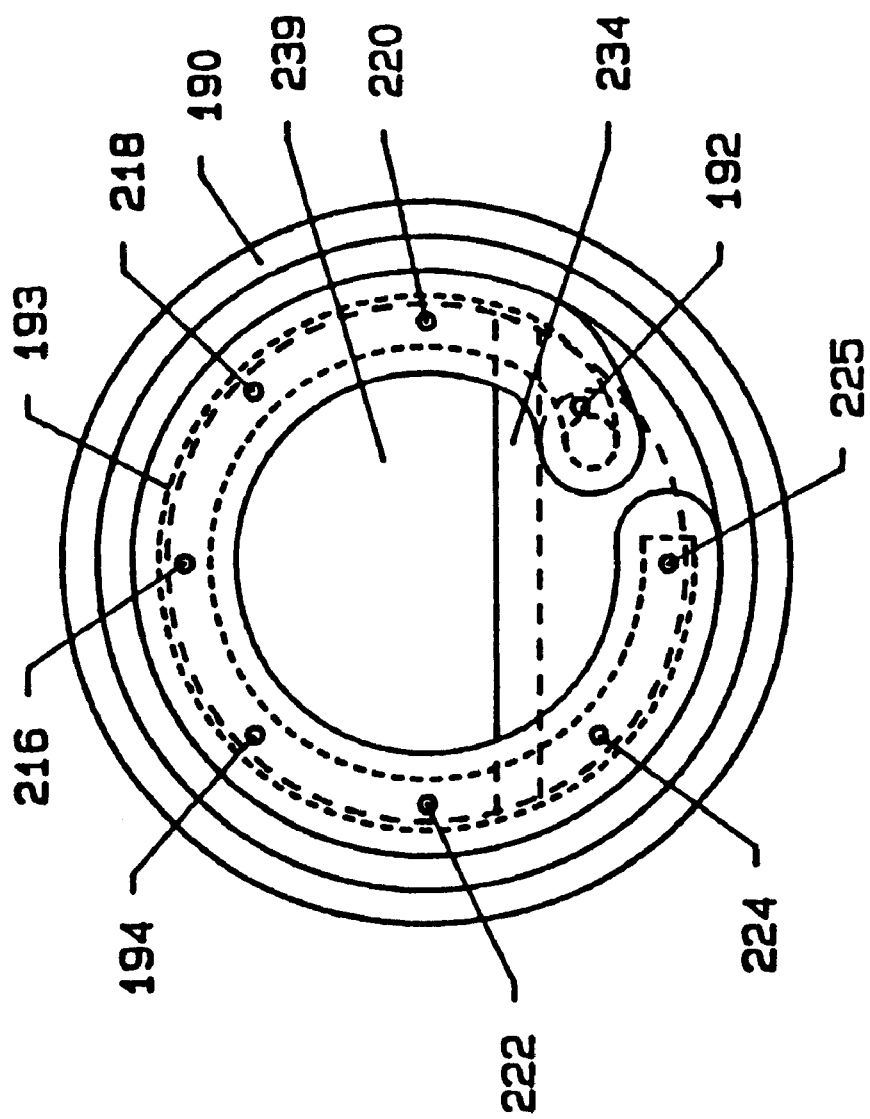
FIG. 14 is a view of the catheter of FIG. 12 taken from the distal end.

FIG. 12 is a partially sectioned view of catheter 228. It is similar in function to catheter 180 except that it has a slightly different lumen configuration. The interior of outer sheath 236 is divided into two lumens by septum 234. The smaller lumen 238 is employed to inflate balloon 190 through inflation port 230. Smaller lumen 238 also contains hypo tubing 208, which becomes the sole use of smaller lumen 238 distal to point 232. The larger lumen 239 is used for a guide wire and evacuation of particulate material. When the larger lumen 239 is used for evacuation, a proximally directed jet 224 is directed as per arrow 227. Particulate material is removed through lumen 239. Jets 194 and 192 are directed distally in the direction of arrows 191 and 195, respectively. Other jets as shown in FIG. 14 can also be directed distally from various points along the jet nozzle assembly 193 (see FIG. 14). All other referenced elements are as previously described.

Figure 13:
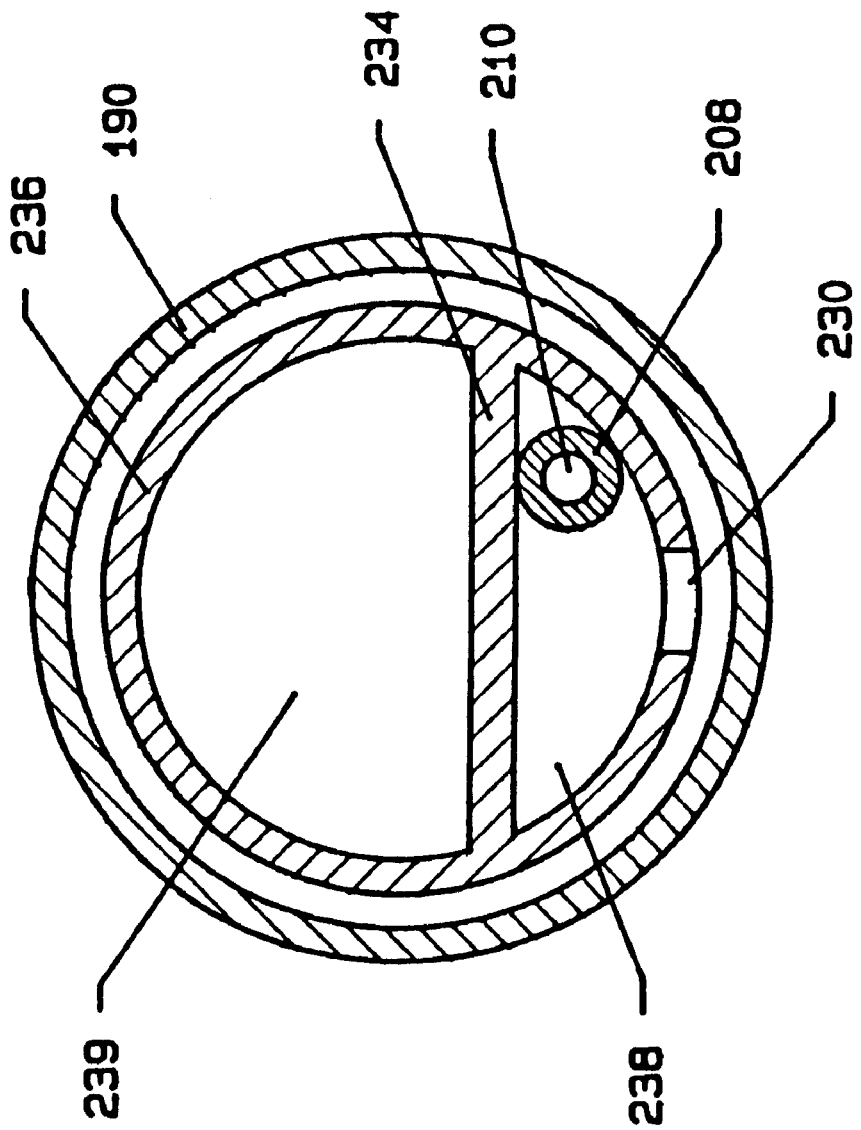
FIG. 13 is a transverse sectioned view of the catheter of FIG. 12 taken across the inflatable balloon.

FIG. 13 is a transverse sectioned view of catheter 228 taken across balloon 190. All referenced elements are as previously described.

FIG. 14 is a view of catheter 228 taken from the distal end. As with catheter 180, multiple jet nozzle assembly 193 provides a number of separate jets supplied from a single source (i.e. hypo tube 208). The jet nozzle assembly 193 can consist of the hypo-tube being bent into a toroidal or arcuate shape as shown. One or more jet(s) may be directed proximally. Orifices 216, 218, 220, 222, 224 and 225 are shown extending through hypo-tube 208 (FIG. 13). All referenced elements are as previously described.

Figure 15:
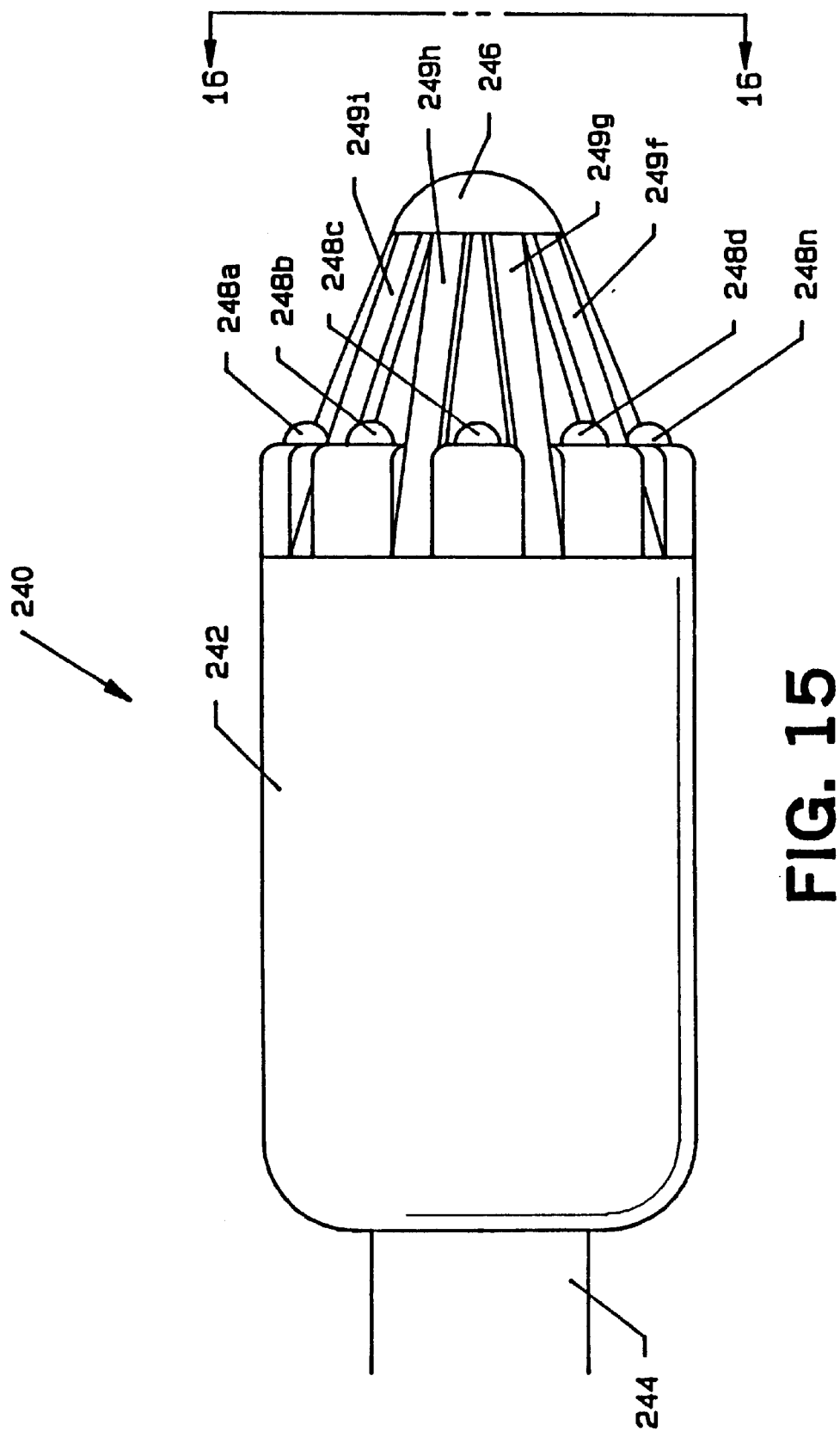
FIG. 15 is a view of the distal end of a guide wire/catheter having multiple jets directed toward the longitudinal axis and forwardly directed ultrasonic transducers located on the tip.

FIG. 15 is a view of the distal end of atherectomy catheter 240. Outer sheath 244 is a flexible polymer which covers a number of separate hypo tubes, each of which feeding a separate jet of multiple nozzle assembly 242. Providing separate supply to each jet permits maximum control of the procedure, as it allows selection of which areas are to be ablated by the corresponding high pressure streams. Each of jets 248a–248n is fabricated similar to the jets previously discussed.

To further control the procedure, a separate ultrasonic transducer may be associated with each of the separately controlled jets. The transducers are located between the jets and are labeled 249a–249n. This enables the attending medical personnel to separately monitor the action of each of the jets. Distal tip 246 is a smooth hemisphere to reduce trauma during insertion.

Figure 16:
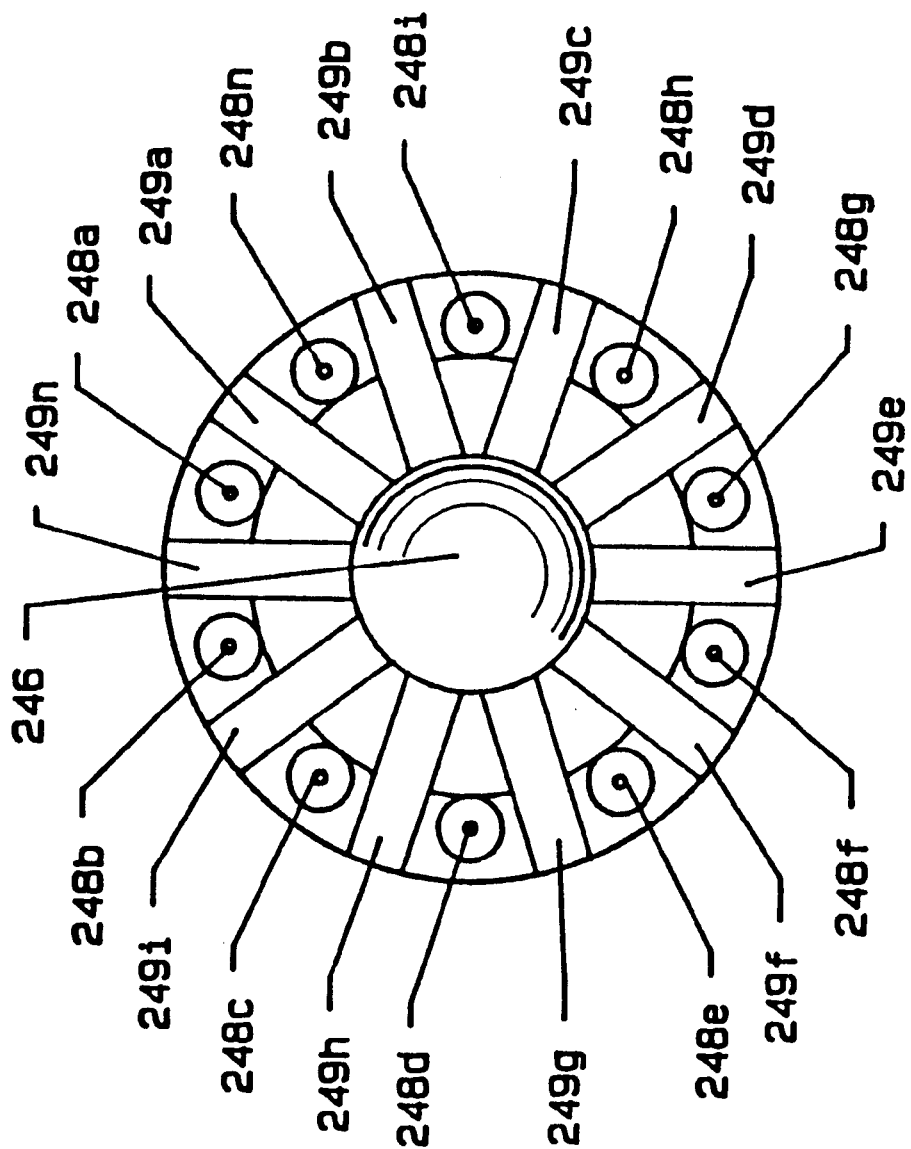
FIG. 16 is an end view of the guide wire/catheter of FIG. 15.

FIG. 16 is a view of atherectomy catheter 240 taken from the distal end. All referenced elements are as previously described.

Figure 17:
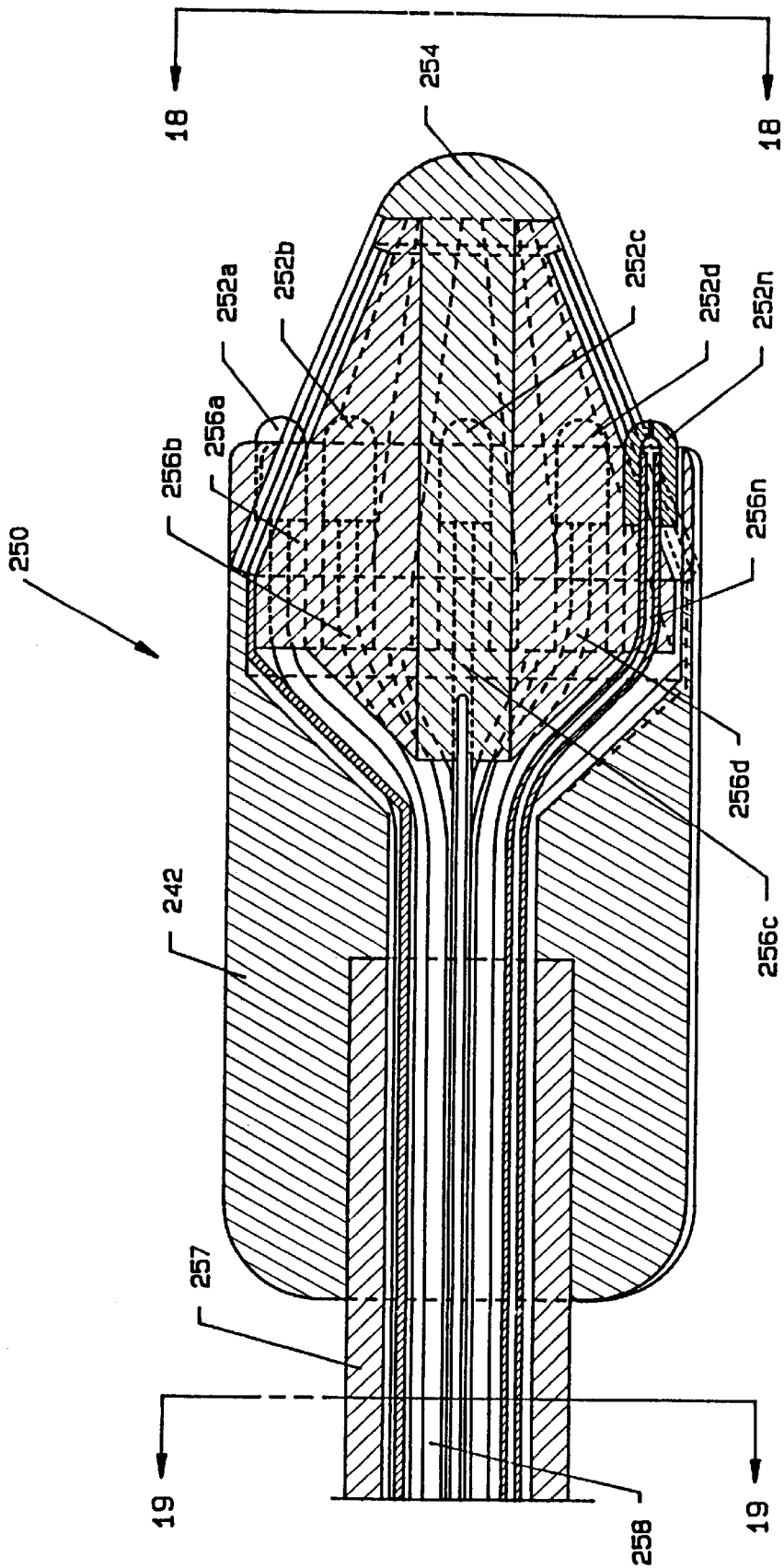
FIG. 17 is a partially sectioned view of the distal end of a catheter having multiple, independently controlled jets.

FIG. 17 is a longitudinal view of catheter 240. The view is partially sectioned and partially in phantom to show coupling of individual hypo tubes 256a–256n to nozzles 252a–252n, respectively. Outer sheath 257 is sealed to end member 251 as shown. Smooth distal tip 254 reduces trauma.

Figure 18:
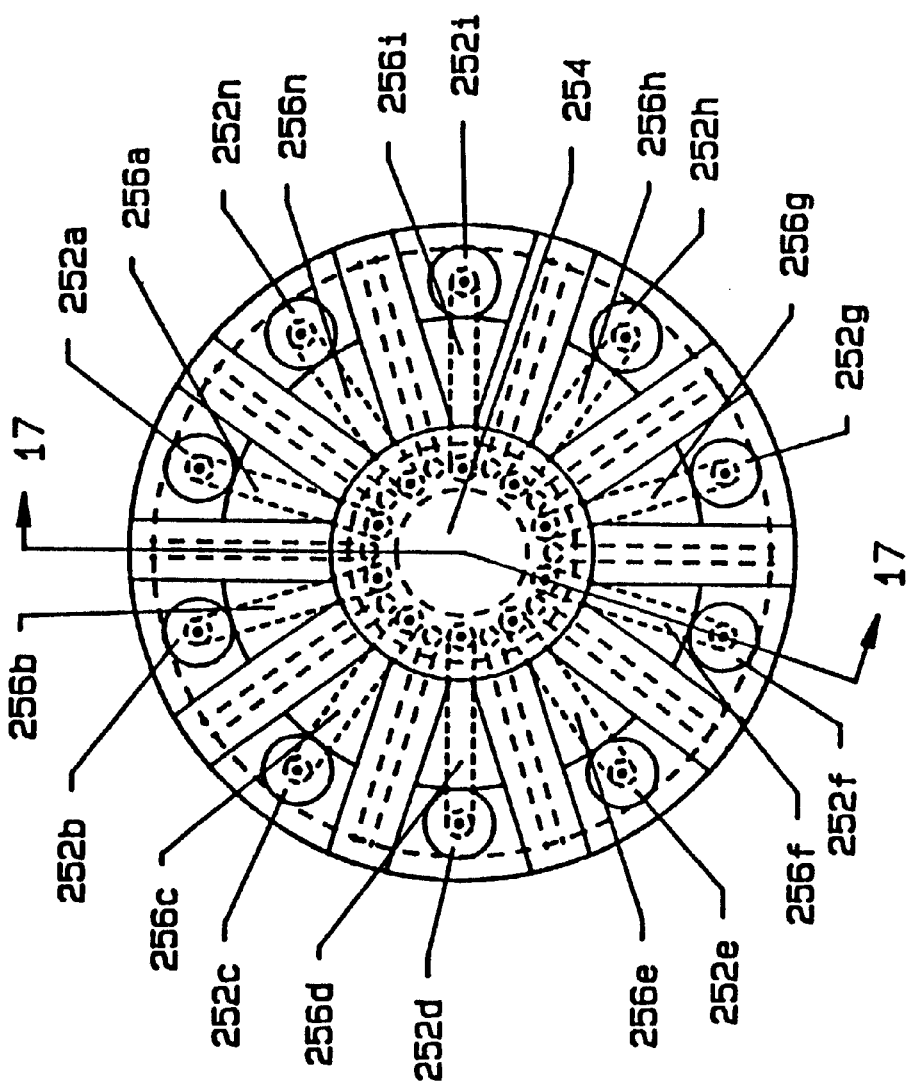
FIG. 18 is an end view of the catheter of FIG. 17.

FIG. 18 is a view of catheter 250 taken from the distal end. All referenced elements are as previously described.

Figure 19:
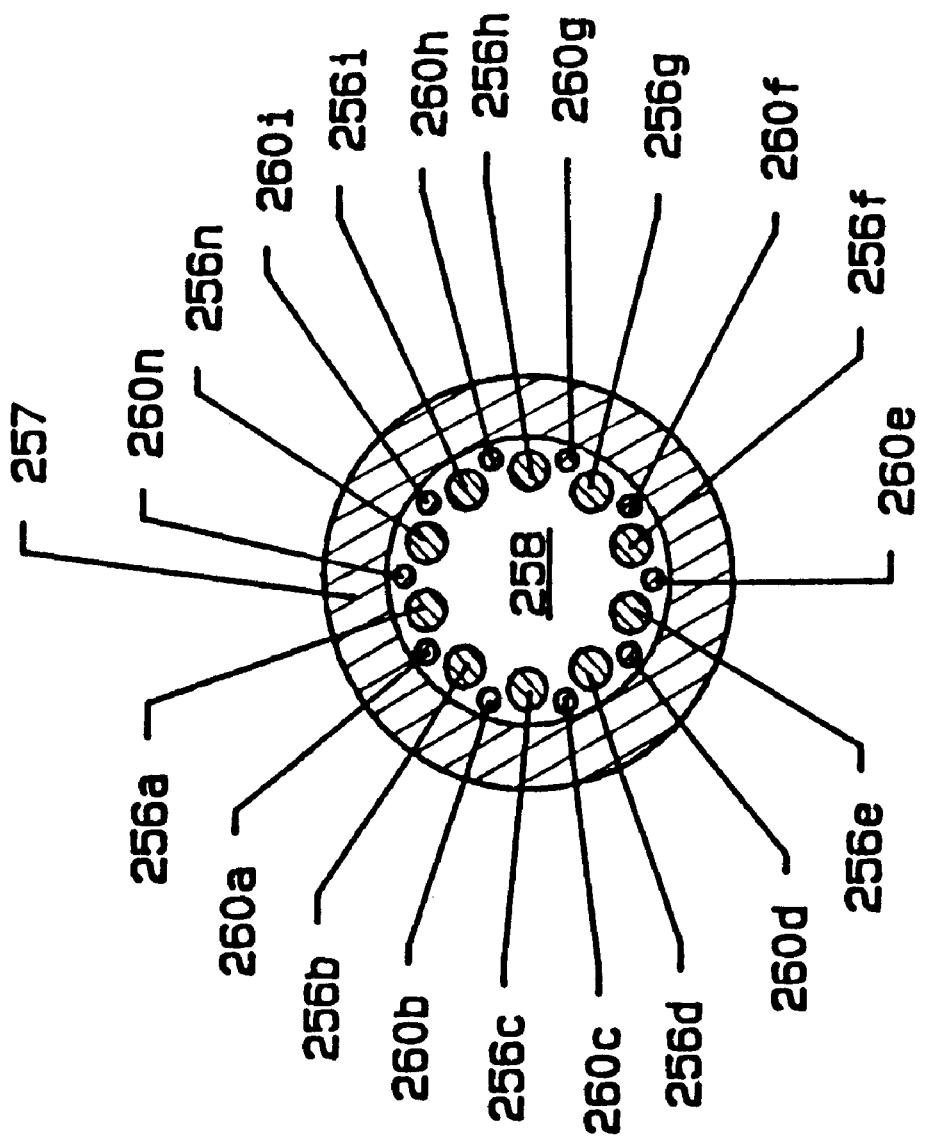
FIG. 19 is a transverse sectioned view of the catheter of FIG. 17 taken proximal of the nozzle assembly.

FIG. 19 is a transverse sectioned view of catheter 250 showing the details of the main catheter body. Hypo tubes 256a–256n are arranged about the inner periphery of outer sheath 257. Interspersed with the typo tubes are individual ultrasonic transducer cables 260a–260n each of which is coupled to the corresponding one of the multiple ultrasonic transducers at the distal tip. In this manner, the attending medical personnel may individually monitor each of the high pressure jets. The remainder of central lumen 258 may be used for evacuation of particulate material.

Figure 20:
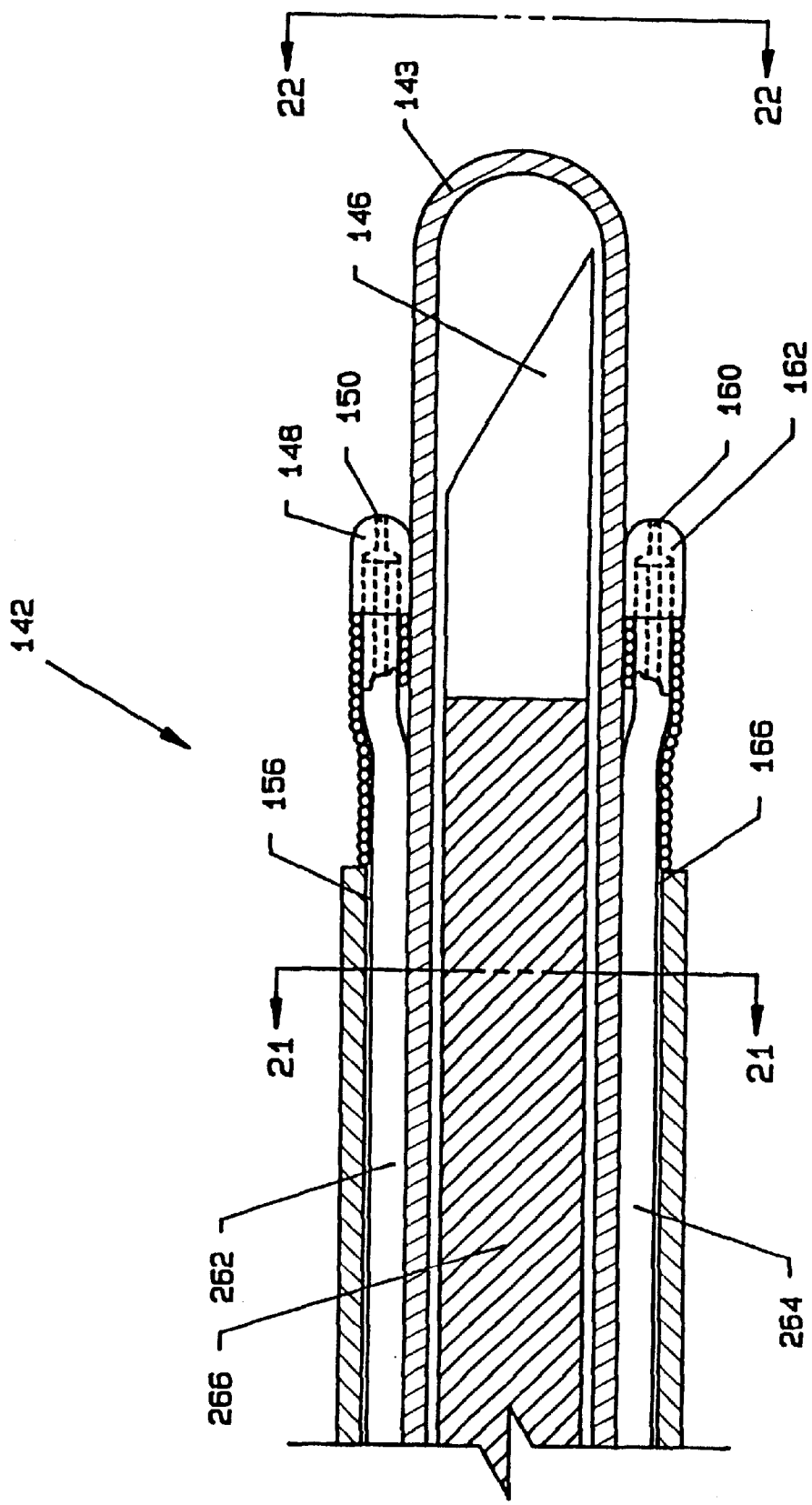
FIG. 20 is a sectioned view of a catheter/guide wire having multiple jets directed parallel to the longitudinal axis and forwardly directed ultrasonic transducers located on the tip.

FIG. 20 is a partially sectioned view of the distal end of catheter 142, which has multiple jets. As explained above, catheter 142 is best suited to enlarge a passage through a deposit wherein the initial passage is sufficiently large to accommodate distal tip 143. Lumen 262 of hypo tubing 156 is isolated from lumen 264 of hypo tubing 166, permitting separate control of jets 150 and 160. The transducer 146 is attached to shaft 266 which is part of the transducer device.

Figure 21:
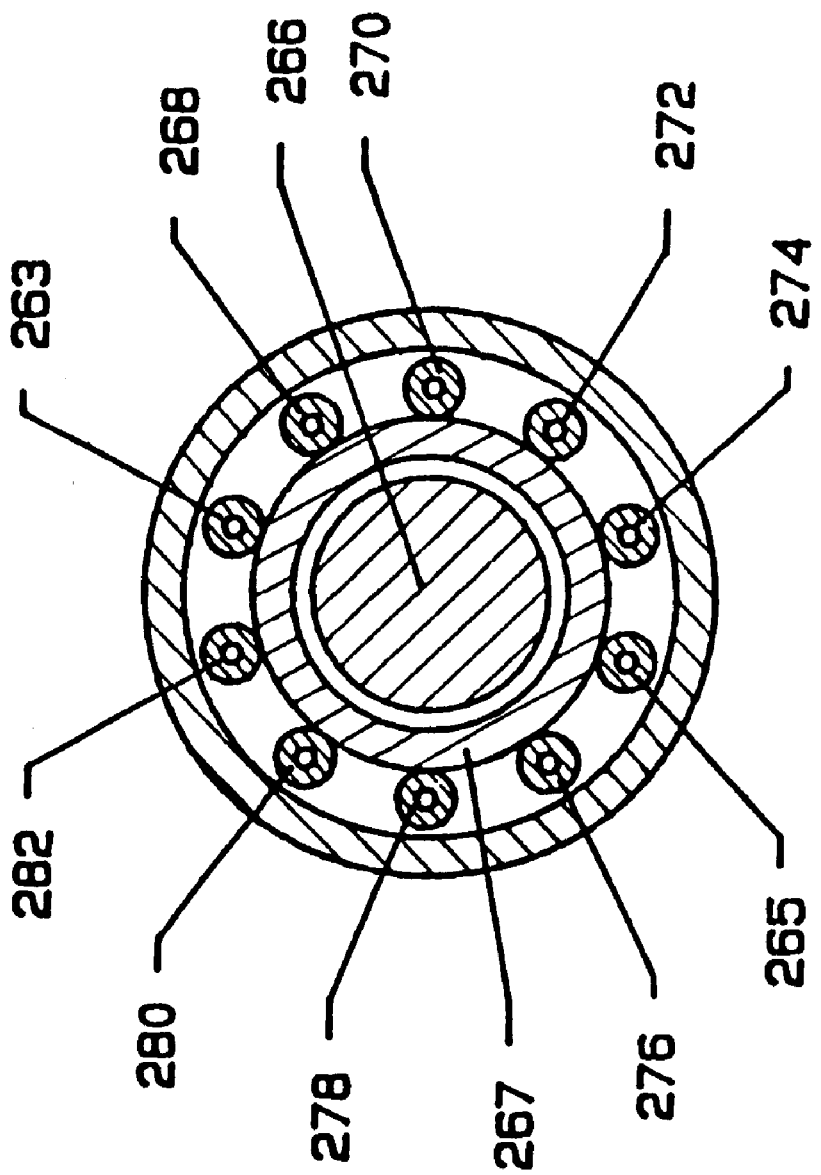
FIG. 21 is a transverse sectioned view of the catheter/guide wire of FIG. 20 taken proximal of the nozzle assemblies.

FIG. 21 is a transverse sectioned view of catheter 142. Individual hypo tubes 263, 265, 268, 270, 272, 274, 276, 278, 280, and 282 each supply a different one of the high pressure jets providing maximum control as described above. The hypo tubes are located about the outer periphery of inner sheath 267. All other referenced elements are as previously described.

Figure 22:
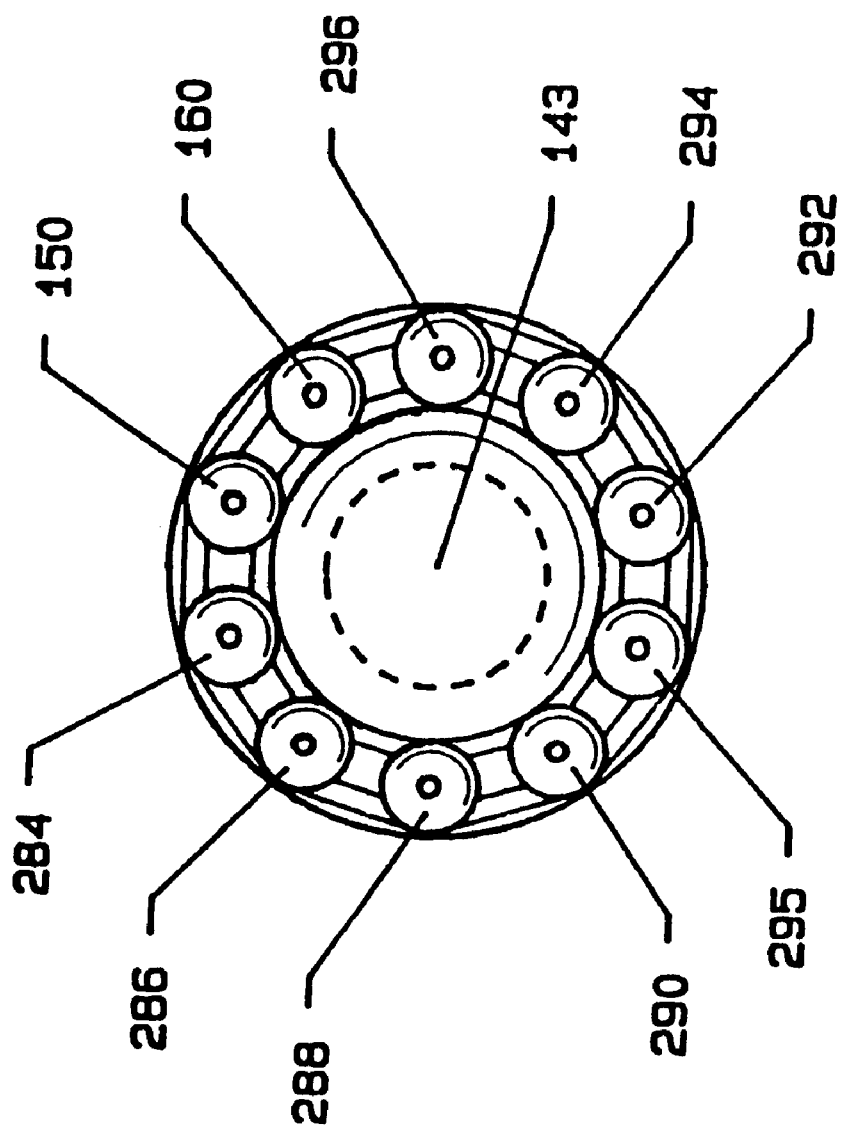
FIG. 22 is a view of the catheter/guide wire of FIG. 20 from the distal end.

FIG. 22 is a view of catheter 142 taken from the distal end. As explained above, jets 150, 160, 295, 296, 292, 290, 288, 286, and 284 are separately controlled from separate hypo tubes (see also FIGS. 20 and 21).

Figure 23:
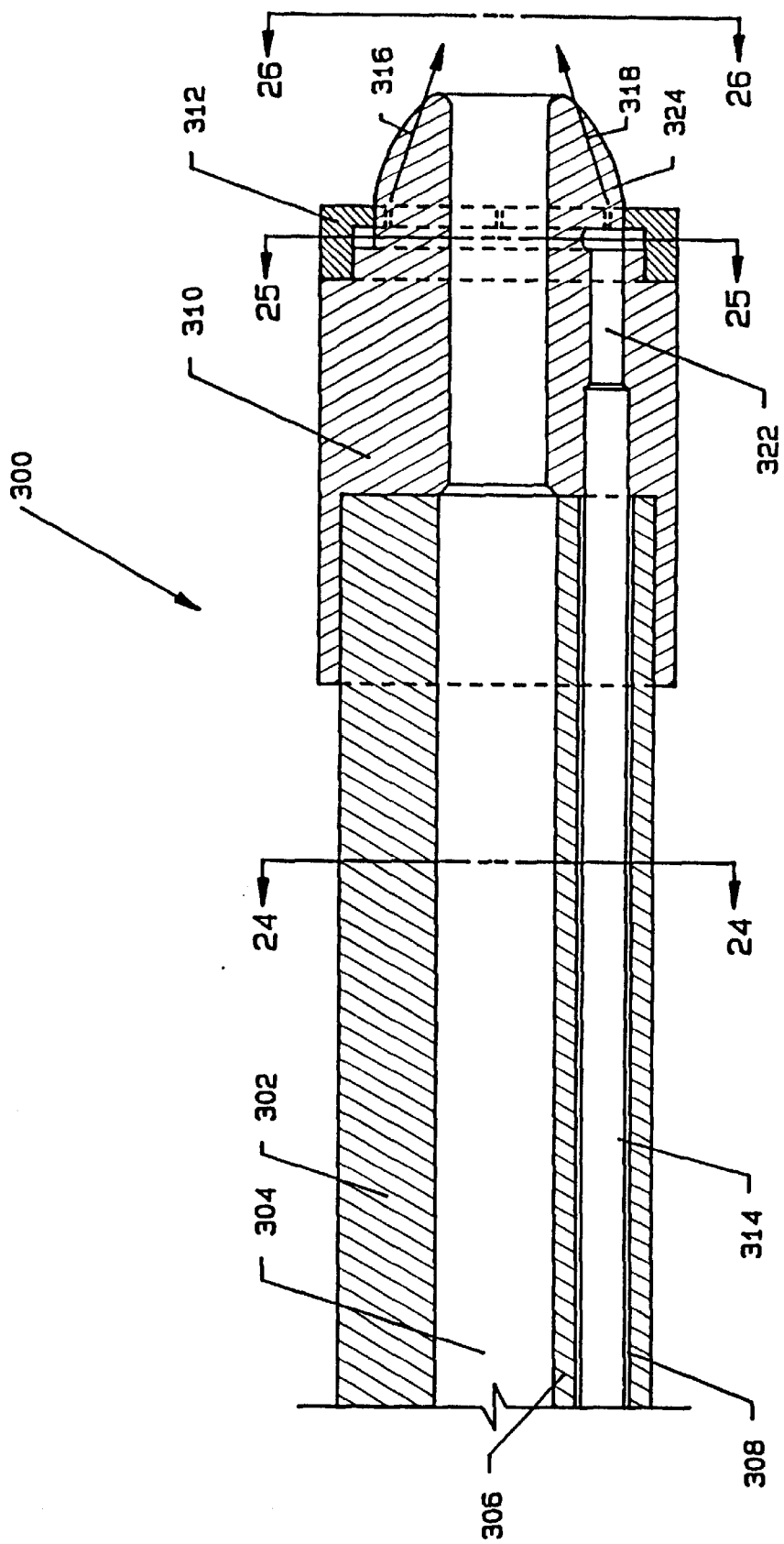
FIG. 23 is a longitudinal sectioned view of the distal end of a catheter having multiple angled jets and a guide wire lumen.

FIG. 23 is a partially sectioned view of catheter 300. This embodiment has multiple jets on nozzle assembly 312 supplied from distal port 322 attached to single hypo tube 314. Outer catheter body 302 has a larger guide wire lumen 304 separated by septum 306 from smaller lumen 308 containing single hypo tube 314.

Distal member 310 is molded to provide attachment of outer catheter body 302 and nozzle assembly 312. Distal member 310 is tapered at point 324 to permit the multipole jets to be angled toward the longitudinal axis as shown by arrows 316 and 318.

Figure 24:
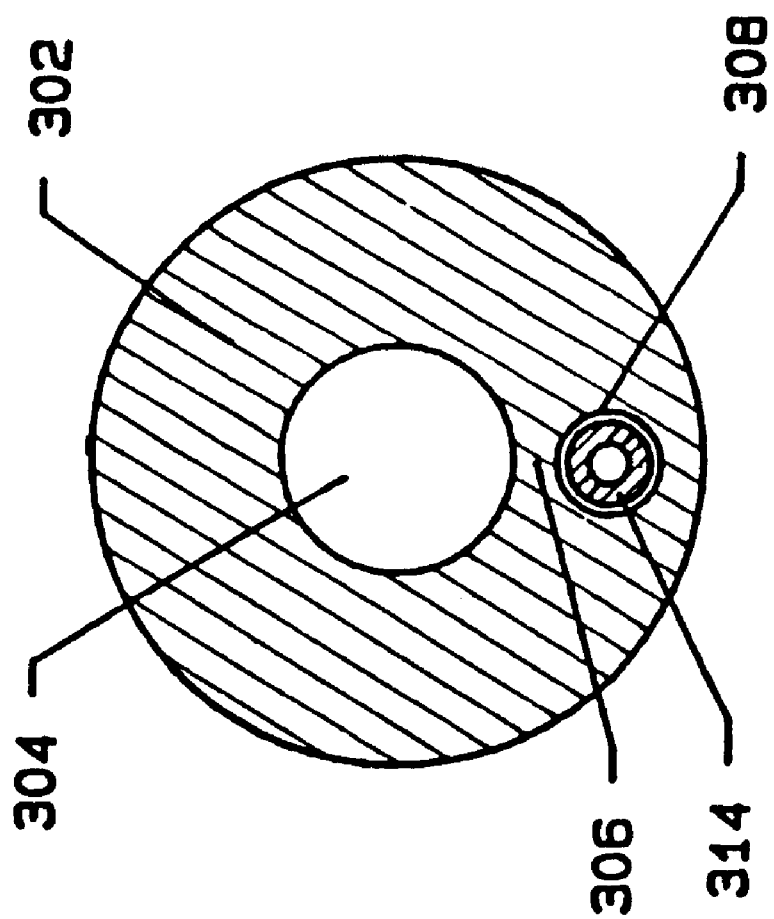
FIG. 24 is a transverse sectioned view of the catheter of FIG. 23 taken proximal to the nozzle assembly.

FIG. 24 is a transverse sectioned view of catheter 300 taken through outer catheter body 302. All referenced elements are as previously described.

Figure 25:
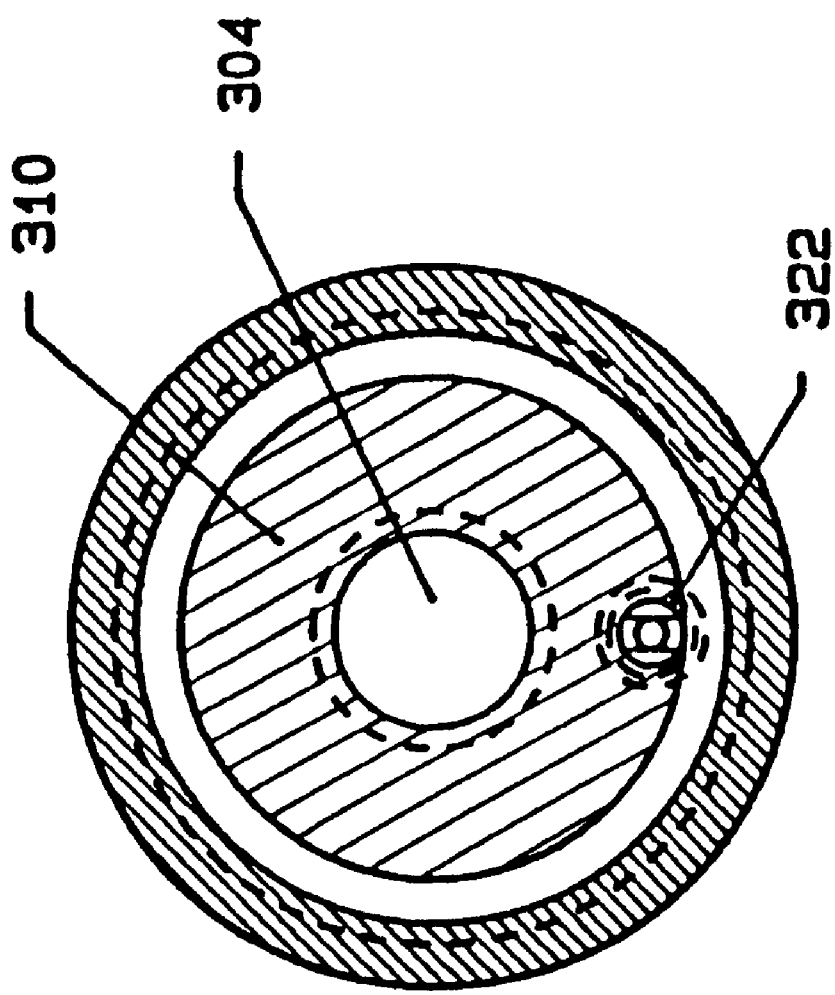
FIG. 25 is a transverse sectioned view of the catheter of FIG. 23 taken distal to FIG. 24.

FIG. 25 is a transverse sectioned view of catheter 300 taken through distal member 310. All referenced elements are as previously described.

Figure 26:
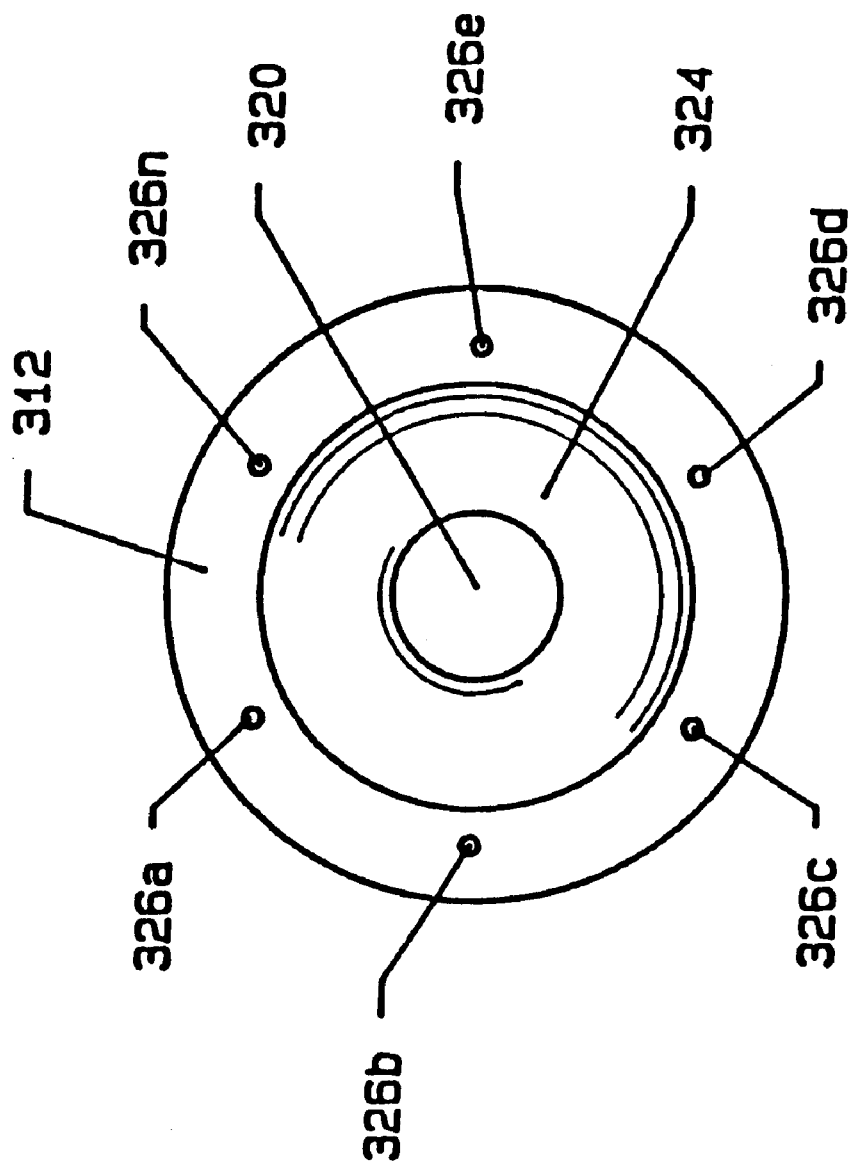
FIG. 26 is a view of the catheter of FIG. 23 taken from the distal end.

FIG. 26 is a view from the distal end of catheter 300. Nozzle assembly 312 contains jets 326a–326n.

Figure 27:
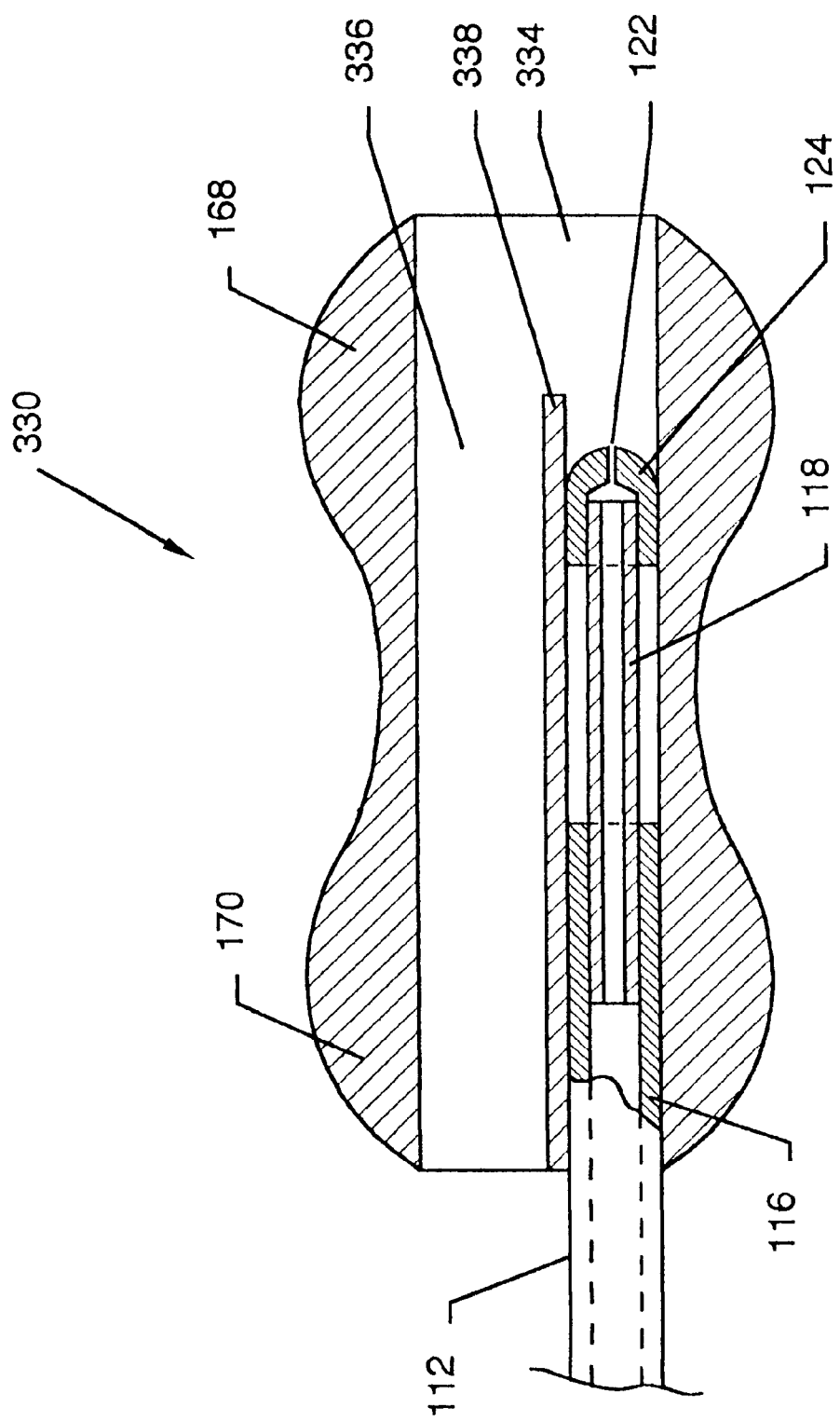
FIG. 27 is a sectioned view of a guide wire having a positioning bulb.

FIG. 27 is a partially sectioned view of a bulbous guide wire 330 having positioning bulbs. The bulb assembly comprising, bulb 168 and bulb 170, is slipped over main body 116 of a guide wire according to the present invention. In the present invention, main body 116 is attached under septum 338. This provides a larger lumen 336 for insertion of a guide wire or another device.

As explained above, use of the structure comprising bulbs 168 and 170 protects the vessel wall from inadvertent abrasion by the high pressure stream produced by jet 122. All other referenced elements are as previously described.

Figure 28:
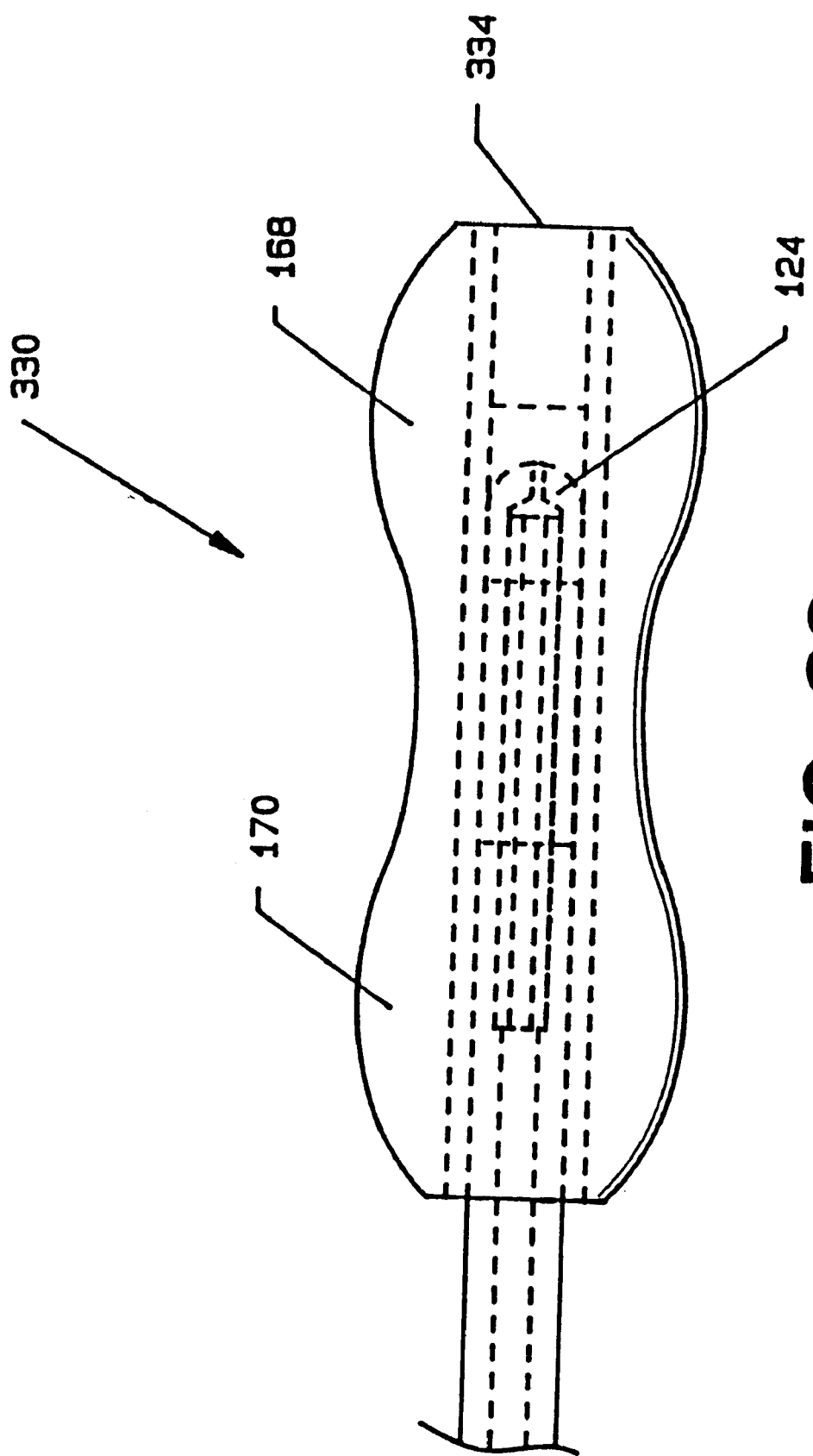
FIG. 28 is a view in partial phantom showing operation of a guide wire having a positioning bulb.

FIG. 28 is a top view in partial phantom of catheter/guide wire 330. All referenced elements are as previously described.

Figure 29:
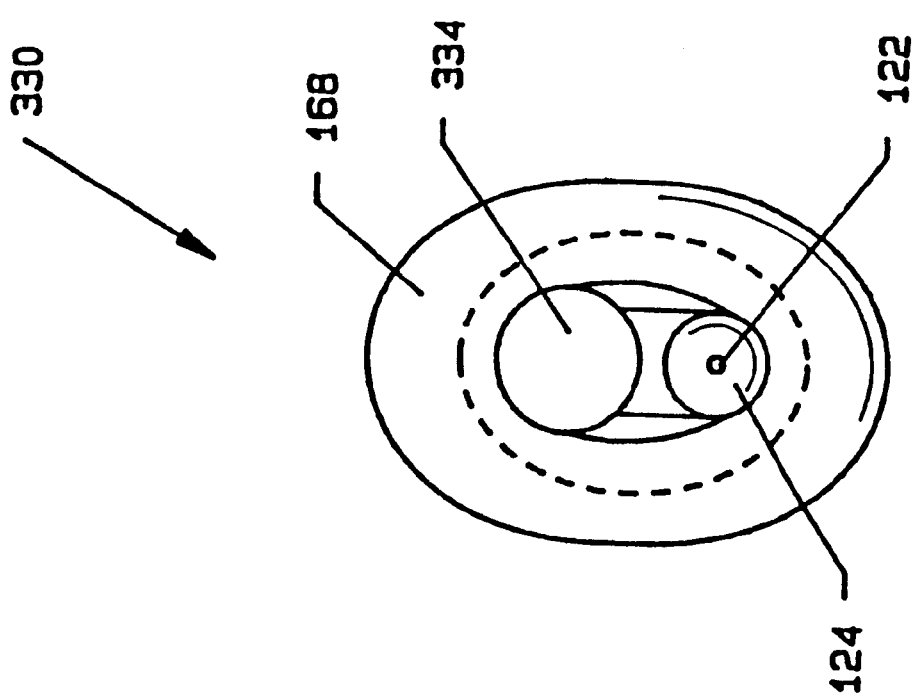
FIG. 29 is a view of the guide wire of FIG. 28 taken from the distal end.

FIG. 29 is a view of catheter/guide wire 330 taken from the distal end. All referenced elements are as previously described.

Figure 30:
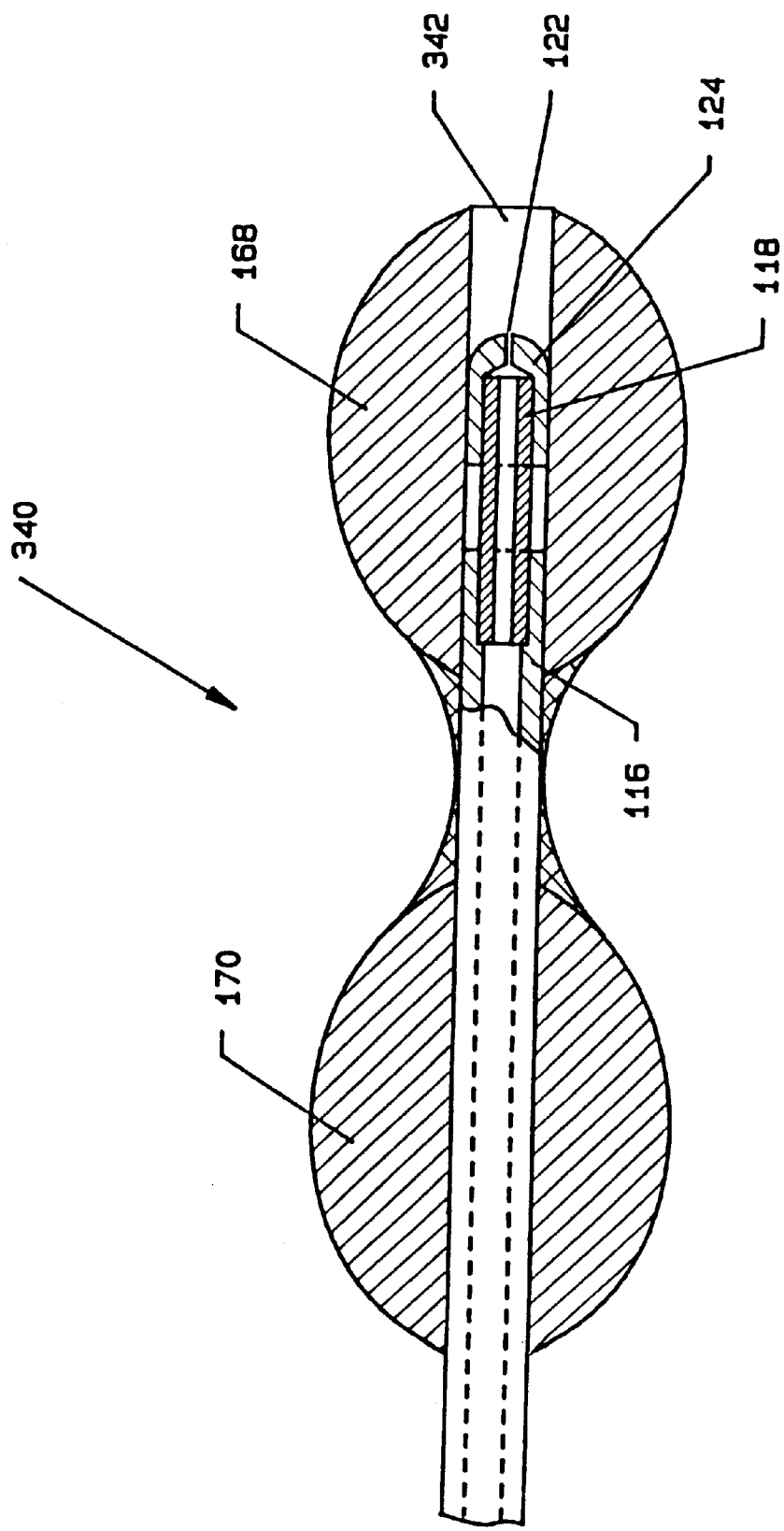
FIG. 30 is a sectioned view of guide wire having multiple positioning bulbs.

FIG. 30 is a partially sectioned view of guide wire 340 having positioning bulbs 168 and 170. Jet 122 directs a high pressure stream distal from lumen 342. Unlike catheter/guide wire 330, guide wire 340 has no separate lumen for another device. All other referenced elements are as previously described.

Figure 31:
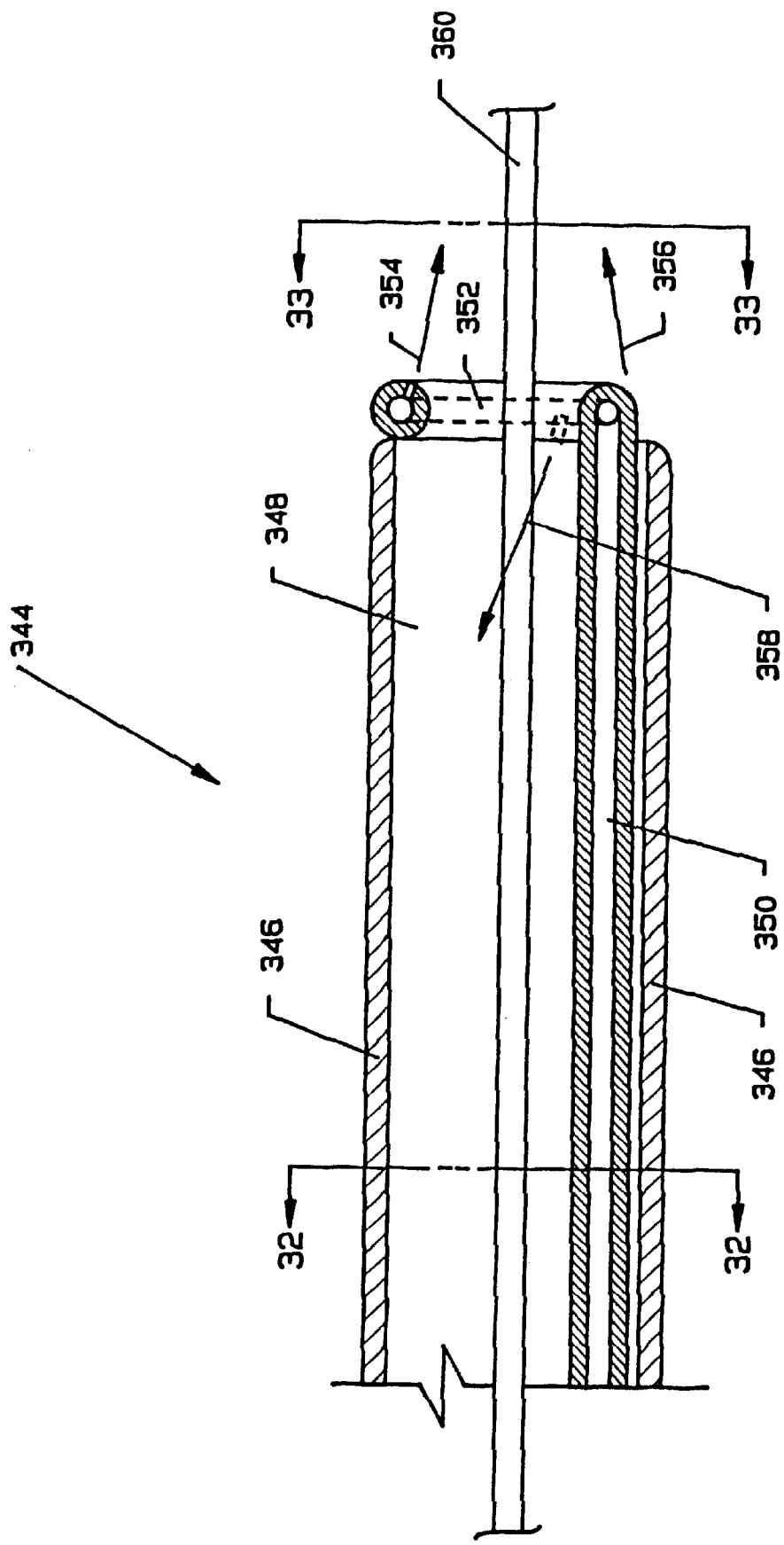
FIG. 31 is a sectional view of the distal end of a catheter having multiple jets directed toward the longitudinal axis.

FIG. 31 is a partially sectioned view of catheter 344. Outer sheath 346 provides a single large lumen 348 which provides for passage of guide wire 360, hypo tubing 350, and evacuation of particulate material. Nozzle assembly 352 has a number of separate jets supplied by single hypo tubing 350. Some of the jets of nozzle assembly 352 may be directed proximally as shown by arrow 358 to encourage rapid evacuation of particulate material. Other jets, though directed distally, are angled toward the central longitudinal axis as shown by arrows 354 and 356.

Figure 32:
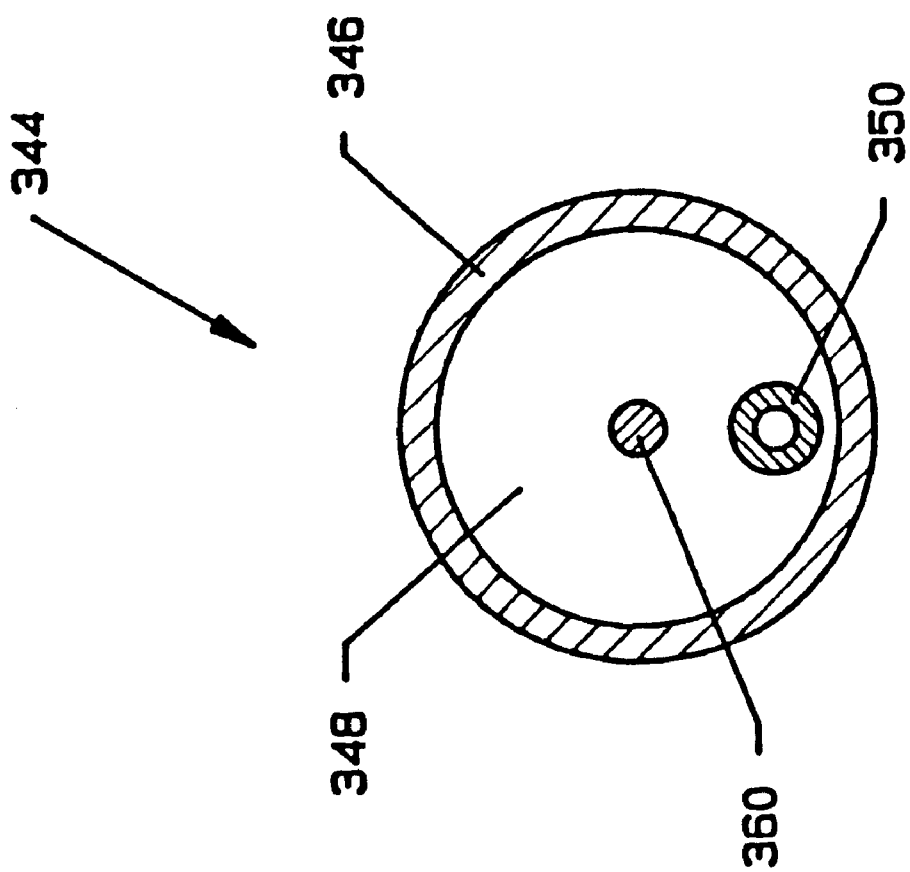
FIG. 32 is a transverse sectioned view of the catheter of FIG. 31.

FIG. 32 is a transverse sectioned view of catheter 344 taken across outer sheath 346. All referenced elements are as previously described.

Figure 33:
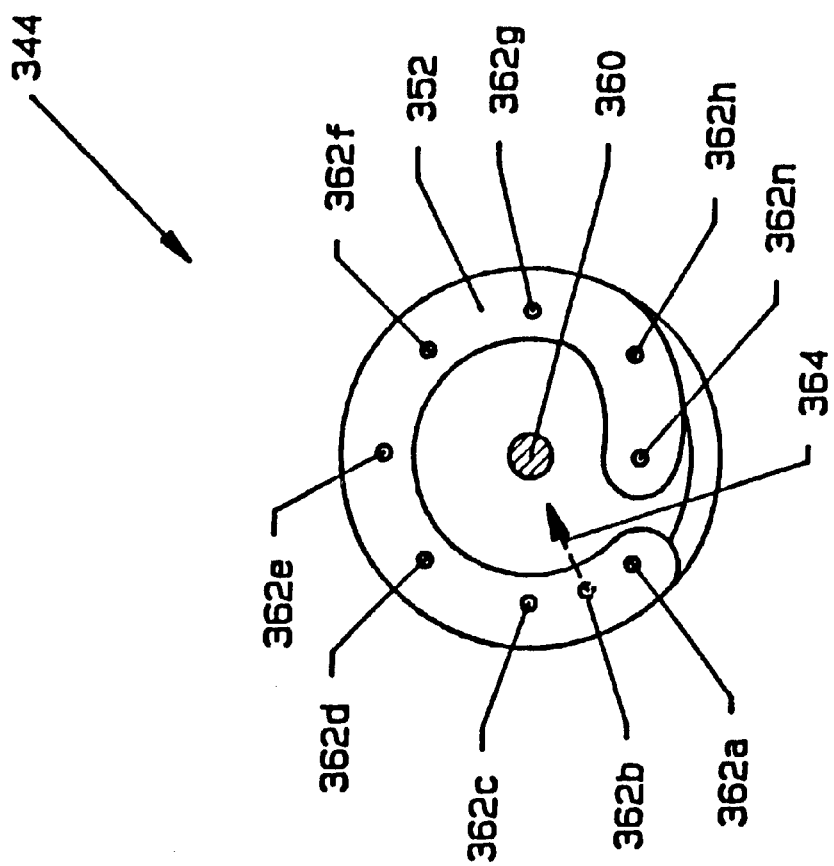
FIG. 33 is a view of the catheter of FIG. 31 taken from the distal end.

FIG. 33 is a view of catheter 344 taken from the distal end. Nozzle assembly 352 has separate jets 362a–362n. Some of the separate jets may be directed toward the central longitudinal access as shown by arrow 364.

Having thus described the preferred embodiments of the present invention, those of skill in the art will readily appreciated that additional embodiments may be made from the teachings found herein within the scope of the claims hereto attached.

We claim:

1. A device with fluid jets for breaking apart tissue or other material in a biological or synthetic body vessel or cavity comprising:

a. a tubular member having a proximal end and a distal end, having a plurality of passages including a first passage and a second passage extending along the length thereof, each passage with a proximal end and a distal end, each passage providing communication between said proximal end and said distal end;

b. said first passage comprising tubular means for carrying a flow of high pressure fluid from said proximal end to said distal end, the distal portion of said tubular means having at least two orifices;

c. said orifice(s) forming fluid jet(s) from the flow of high pressure fluid, at least one of the fluid jets being directed by said orifice(s) to impinge upon the tissue;

d. at least one of said orifices directing at least one of the fluid jets in a direction which is largely distal to said distal end of said first passage;

e. said proximal end of said first passage having means to connect to a high pressure fluid source which drives a flow of fluid into said first passage;

f. said second passage provides for passage of fluid between said distal end and said proximal end, said distal end of said second passage having an opening; and g. at least one of said orifices directing at least one fluid jet emanating from said distal end of said tubular means to impinge on said opening in said distal end of said second passage.

2. The device of claim 1, wherein said first passage is connected to a high pressure fluid source that supplies fluid to said tubular means at a pressure greater than approximately 5000 psi.

3. The device of claim 1, wherein at least one of said orifices directs at least one jet emanating from said distal end of said tubular means to impinge on said opening in said distal end of said second passage, and to provide stagnation pressure which tends to drive a flow of fluid and emulsified tissue from said distal end of said second passage towards said proximal end of said second passage, thereby aiding in the removal of emulsified tissue from the body vessel.

4. The device of claim 3, wherein said first passage is connected to a high pressure fluid source that supplies fluid to said tubular means at a pressure greater than approximately 5000 psi.

5. The device of claim 1, wherein at least one of said orifices directs at least one jet emanating from said distal end of said tubular means to impinge on said opening in said distal end of said second passage, and to provide stagnation pressure which is sufficient to drive a flow of fluid and emulsified tissue from said distal end of said second passage towards said proximal end of said second passage, thereby providing removal of emulsified tissue from the body vessel, and channel particulate or emulsified material toward said distal end of said second passage.

6. The device of claim 5, wherein said first passage is connected to a high pressure fluid source that supplies fluid to said tubular means at a pressure greater than approximately 5000 psi.

7. The device of claim 3, 5 or 6, wherein said proximal end of said second passage is connected to a metering means to control the flow of fluid and emulsified tissue along said second passage at a rate of flow less than the rate of flow which would result without said metering means.

8. The device of claim 7, wherein the proximal end of said second passage is connect to a roller pump which controls the outflow resistance in said second passage and hence the roller pump controls the flow of emulsified tissue along said second passage.

9. The device of claim 7, wherein said proximal end of said second passage is connected to a metering means to control the rate of flow of fluid and emulsified tissue in said second passage and thereby controls a net volume infusion.

10. The device of claim 3, 5 or 6, wherein said proximal end of said second passage is connected to a suction means to augment the flow of fluid and emulsified tissue along said second passage.

11. The device of claim 10, wherein said proximal end of said second passage is connected to a suction means to provide control of the rate of flow of fluid and emulsified tissue in said second passage to control a net volume infusion.

12. The device of claim 1, wherein said tubular means of said first passage carries a flow of high pressure fluid at a pressure greater than approximately 5000 psi to said distal end of said first passage.

13. The device of claim 1, 5 or 6, wherein at least one of said orifices directs at least one fluid jet primarily parallel to a longitudinal axis of said tubular member.

14. The device of claim 1, 5 or 6, wherein at least one of said orifices directs at least one fluid jet emanating from said distal end of said tubular means primarily nonparallel to a longitudinal axis of said tubular member.

15. The device of claim 1, 5 or 6, wherein said second passage provides passage for a catheter device taken from a list comprising a guidewire, ultrasound catheter, angioscopic catheter, and balloon catheter.

16. The device of claim 1, 5 or 6, wherein said first passage is connected to a high pressure fluid source that comprises a positive displacement piston pump.

17. The device of claim 16, wherein said tubular means carries a flow of high pressure fluid in a largely pulsatile or periodic unsteady flow.

18. The device of claim 16, wherein said tubular means carries a flow of high pressure fluid in a largely steady flow.

19. The device of claim 1, 5 or 6, wherein said distal end of said tubular mean is formed into an arcuate shape.

20. The device of claim 1, 5 or 6, wherein said distal end of said tubular means is formed into a toroidal shape which is oriented in a plane perpendicular to a longitudinal axis of said tubular member.

21. The device of claim 1, 5 or 6, wherein a plurality of said orifices direct a plurality of jets along said distal end of said first passage; when a guidewire device is in position at said distal end of said tubular member, said plurality of orifices decrease any effect that the guidewire may have in shielding any tissue from the plurality of jets directed by said orifices.

22. The device of claim 1, 5 or 12, further comprising a multiple jet nozzle assembly at said distal end of said tubular means which provides high pressure fluid from said distal end of said tubular means to a plurality of said orifices.

23. The device of claim 1, 5 or 12, wherein said tubular means comprises a high strength tube constructed of a high strength material taken from a group comprising metal, high strength polymer, and polyimide.

24. A device with fluid jets for breaking apart and removing tissue or other material from a biological or synthetic body vessel or cavity comprising:
   a. a tubular member having a proximal end and a distal end, having a plurality of passages including a first passage and a second passage extending along the length thereof, each passage with a proximal end and a distal end, each passage providing communication between said proximal end and said distal end;
   b. said first passage comprising tubular means for carrying a flow of high pressure fluid from said proximal end to said distal end, the distal portion of said tubular means having one or more orifices;
   c. said orifice(s) forming fluid jet(s) from the flow of high pressure fluid, at least one of the fluid jets being directed by said orifice(s) to impinge upon the tissue;
   d. at least one of said orifices directing at least one of the fluid jets in a direction which is largely distal to said distal end of said first passage;
   e. said proximal end of said first passage having means for connection to a high pressure fluid source which drives a flow of fluid into said tubular means, the high pressure fluid source providing fluid to said tubular means at a pressure between approximately 500 psi and 5000 psi for treatment of relatively softer material;
   f. said second passage provides for removal of fluid and emulsified tissue from said distal end to said proximal end, said distal end of said second passage having an opening; and
   g. at least one of said orifices directing at least one fluid jet emanating from said distal end of said tubular means to impinge on said opening in said distal end of said second passage.

25. A device with fluid jets for breaking apart and removing tissue or other material from a biological or synthetic body vessel or cavity comprising:
   a. a tubular member having a proximal end and a distal end, having a plurality of passages including a first passage and a second passage extending along the length thereof, each passage with a proximal end and a distal end;
   b. said first passage comprising tubular means for carrying high pressure fluid from said proximal end to said distal end, the distal portion of said tubular means having at least two orifices;
   c. said orifices forming fluid jets from the flow of high pressure fluid, at least one of the fluid jets being directed by said orifice(s) to impinge upon the tissue;
   d. at least one of said orifices directing at least one fluid jet in a direction which is largely distal to said distal end of said first passage;
   e. said proximal end of said first passage is connected to a high pressure fluid source which drives a flow of fluid into said tubular means;

f. said second passage provides for passage of a catheter device, said distal end of said second passage having an opening; and, g. at least one of said orifices directing at least one fluid jet emanating from said distal end of said tubular means to impinge on said opening in said distal end of said second passage.

26. The device of claim 25, further comprising a jet nozzle assembly at said distal end of said tubular means which provides the high pressure fluid from said first passage to said orifices.

27. The device of claim 25, wherein at least one of said orifices direct at least one fluid jet emanating from said distal end of said tubular means in a direction approximately parallel to the axis of said tubular member.

28. The device of claim 25, wherein at least one of said orifices which direct fluid jet(s) emanating from said distal end of said tubular means is directed nonparallel to a longitudinal axis of said tubular member.

29. The device of claim 25, wherein said proximal end of said second passage is connected to a metering means to control a flow of fluid and emulsified tissue along said second passage at a rate of flow less than the rate of flow which would result without said metering means.

30. The device of claim 25, wherein said proximal end of said second passage is connected to a suction means to augment a flow of fluid and emulsified tissue along said second passage.

31. The device of claim 25, wherein a plurality of said orifices are positioned along said distal end of said tubular means; when a catheter device is in position at said distal end of said tubular member, said plurality of orifices are not shielded from the tissue by the guidewire or other catheter device.

* * * * *